(12) United States Patent
Remmers et al.

(10) Patent No.: US 8,783,260 B2
(45) Date of Patent: Jul. 22, 2014

(54) APPARATUSES AND METHODS FOR MANDIBULAR PROTRUSION

(75) Inventors: John E. Remmers, Sedona, AZ (US); Hugo Tam, Calgary (CA); Terry Macartney, Calgary (CA); Peter Santosham, Calgary (CA)

(73) Assignee: ZST Holdings Inc., Calgary, Alberta (CA)

( * ) Notice: Subject to any disclaimer, the term of this patent is extended or adjusted under 35 U.S.C. 154(b) by 125 days.

(21) Appl. No.: 12/794,555

(22) Filed: Jun. 4, 2010

(65) Prior Publication Data

US 2010/0316973 A1    Dec. 16, 2010

Related U.S. Application Data

(60) Provisional application No. 61/184,440, filed on Jun. 5, 2009.

(51) Int. Cl.
*A61F 5/56* (2006.01)

(52) U.S. Cl.
USPC .......................... 128/848; 128/861; 128/862

(58) Field of Classification Search
CPC .................................. A61F 5/56; A61F 5/566
USPC .................. 128/848, 859, 861–862; 602/902; 433/6–7
See application file for complete search history.

(56) References Cited

U.S. PATENT DOCUMENTS

| | | | |
|---|---|---|---|
| 2,171,695 A | 9/1939 | Harper | |
| 4,376,628 A * | 3/1983 | Aardse | 433/80 |
| 4,602,905 A * | 7/1986 | O'Keefe, III | 433/41 |
| 4,901,737 A | 2/1990 | Toone | 128/848 |
| 5,030,098 A * | 7/1991 | Branford | 433/215 |
| 5,154,609 A | 10/1992 | George | |
| 5,313,960 A | 5/1994 | Tomasi | 128/848 |
| 5,365,945 A | 11/1994 | Halstrom | 128/848 |
| 5,409,017 A | 4/1995 | Lowe | 128/848 |
| 5,427,117 A | 6/1995 | Thornton | 128/848 |
| 5,513,986 A * | 5/1996 | Feltham et al. | 433/91 |
| 5,537,994 A | 7/1996 | Thornton | 128/204.18 |
| 5,566,683 A | 10/1996 | Thornton | 128/848 |
| 5,570,704 A | 11/1996 | Buzzard et al. | 128/848 |
| 5,611,355 A | 3/1997 | Hilsen | 128/848 |

(Continued)

FOREIGN PATENT DOCUMENTS

| | | |
|---|---|---|
| EP | 1 832 306 | 9/2007 |
| WO | 2013/102095 | 7/2013 |
| WO | 2013/188660 | 12/2013 |

OTHER PUBLICATIONS

International Search Report issued in PCT/US2010/037475, dated Jan. 4, 2011.

(Continued)

*Primary Examiner* — Patricia Bianco
*Assistant Examiner* — Camtu Nguyen
(74) *Attorney, Agent, or Firm* — Meunier, Carlin & Curfman, LLC

(57) ABSTRACT

Embodiments of methods and mandibular protruders and positioning devices, comprising, for example: an upper mounting bracket having an upper dental appliance; a lower mounting bracket having a lower dental appliance; and a rail system configured to couple the upper mounting bracket to the lower mounting bracket. Some embodiments comprise a drive motor and/or an initial position adjustment mechanism.

16 Claims, 19 Drawing Sheets

(56) References Cited

U.S. PATENT DOCUMENTS

| | | | |
|---|---|---|---|
| 5,642,737 A | 7/1997 | Parks | 128/848 |
| 5,666,960 A | 9/1997 | Fredberg et al. | |
| 5,678,567 A | 10/1997 | Thornton et al. | 128/848 |
| 5,755,219 A | 5/1998 | Thornton | 128/201.18 |
| 5,794,627 A | 8/1998 | Frantz et al. | 128/848 |
| 5,816,799 A | 10/1998 | Parker | 433/6 |
| 5,823,193 A | 10/1998 | Singer et al. | 128/848 |
| 5,826,579 A | 10/1998 | Remmers et al. | 128/848 |
| 5,829,441 A | 11/1998 | Kidd | |
| 5,846,212 A * | 12/1998 | Beeuwkes et al. | 601/38 |
| 5,868,138 A | 2/1999 | Halstrom | 128/848 |
| 5,884,628 A | 3/1999 | Hilsen | 128/848 |
| 5,921,942 A | 7/1999 | Remmers et al. | 600/529 |
| 5,941,247 A * | 8/1999 | Keane | 128/848 |
| 5,954,048 A | 9/1999 | Thornton | 128/201.18 |
| 5,983,892 A | 11/1999 | Thornton | 128/201.26 |
| 6,012,920 A * | 1/2000 | Woo | 433/19 |
| 6,041,784 A | 3/2000 | Halstrom | 128/848 |
| 6,055,986 A | 5/2000 | Meade | 128/848 |
| 6,109,265 A | 8/2000 | Frantz et al. | 128/848 |
| 6,155,262 A | 12/2000 | Thornton et al. | 128/859 |
| 6,161,542 A | 12/2000 | Halstrom | 128/848 |
| 6,273,859 B1 | 8/2001 | Remmers et al. | 600/529 |
| 6,305,376 B1 | 10/2001 | Thornton | 128/848 |
| 6,325,064 B1 | 12/2001 | Thornton | 128/204.18 |
| 6,374,824 B1 | 4/2002 | Thornton | |
| 6,516,805 B1 | 2/2003 | Thornton | 128/848 |
| 6,634,353 B1 | 10/2003 | Knebelman et al. | 128/200.24 |
| 6,729,335 B1 | 5/2004 | Halstrom | 128/848 |
| 6,769,910 B1 | 8/2004 | Pantino | 433/6 |
| 6,877,513 B2 | 4/2005 | Scarberry et al. | 128/848 |
| 7,146,982 B2 | 12/2006 | Mousselon et al. | 128/848 |
| 7,174,895 B2 | 2/2007 | Thornton et al. | 128/848 |
| 7,328,698 B2 * | 2/2008 | Scarberry et al. | 128/200.24 |
| 7,328,705 B2 | 2/2008 | Abramson | 128/848 |
| 7,331,349 B2 | 2/2008 | Brady et al. | 128/848 |
| 7,357,635 B2 | 4/2008 | Belfor et al. | 433/24 |
| 7,637,262 B2 | 12/2009 | Bailey | |
| 7,832,403 B2 | 11/2010 | Halstrom et al. | |
| 8,025,063 B2 | 9/2011 | Sotos et al. | |
| 8,037,886 B2 | 10/2011 | Sotos et al. | |
| 8,226,407 B2 * | 7/2012 | Hanewinkel et al. | 433/140 |
| 2005/0028827 A1 * | 2/2005 | Halstrom | 128/861 |
| 2005/0081859 A1 | 4/2005 | Scarberry et al. | 128/206 |
| 2005/0175954 A1 | 8/2005 | Zacher | 433/5 |
| 2006/0003292 A1 | 1/2006 | Lauren et al. | |
| 2007/0068534 A1 | 3/2007 | Bailey et al. | |
| 2007/0283967 A1 * | 12/2007 | Bailey | 128/848 |
| 2008/0076094 A1 | 3/2008 | Hindin | |
| 2009/0241969 A1 | 10/2009 | Walker | |
| 2010/0154802 A1 | 6/2010 | Fuselier | |
| 2011/0232652 A1 | 9/2011 | Levendowski | |

OTHER PUBLICATIONS

International Preliminary Report on Patentability issued in PCT/US2010/037475, dated Dec. 15, 2011.

International Search Report, dated May 15, 2013, received in connection with related International Application No. PCT/US2012/072093.

* cited by examiner

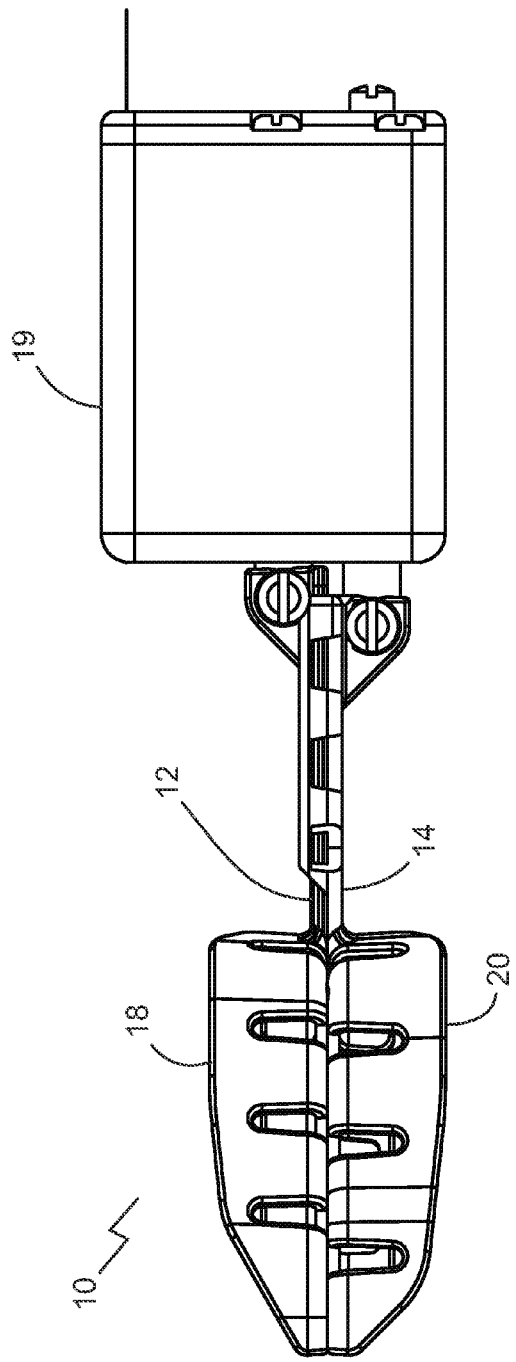
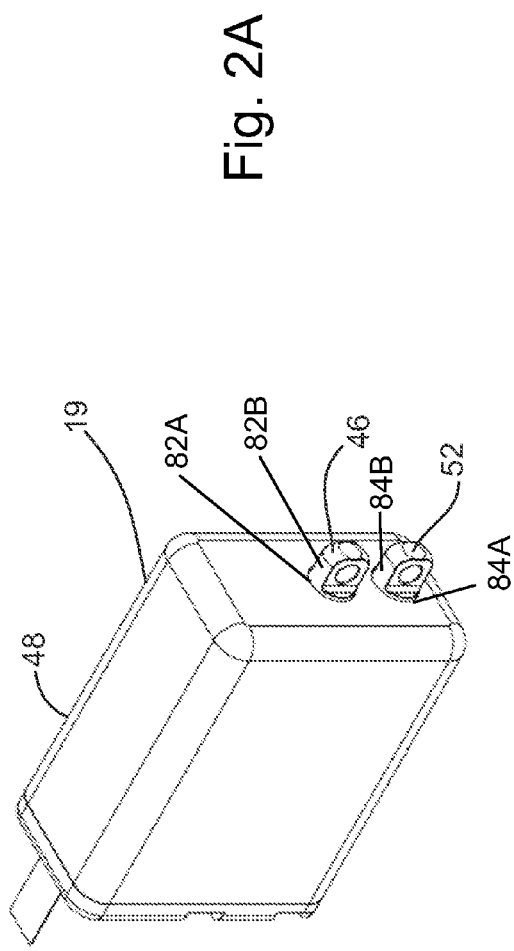
Fig. 2
Fig. 2A

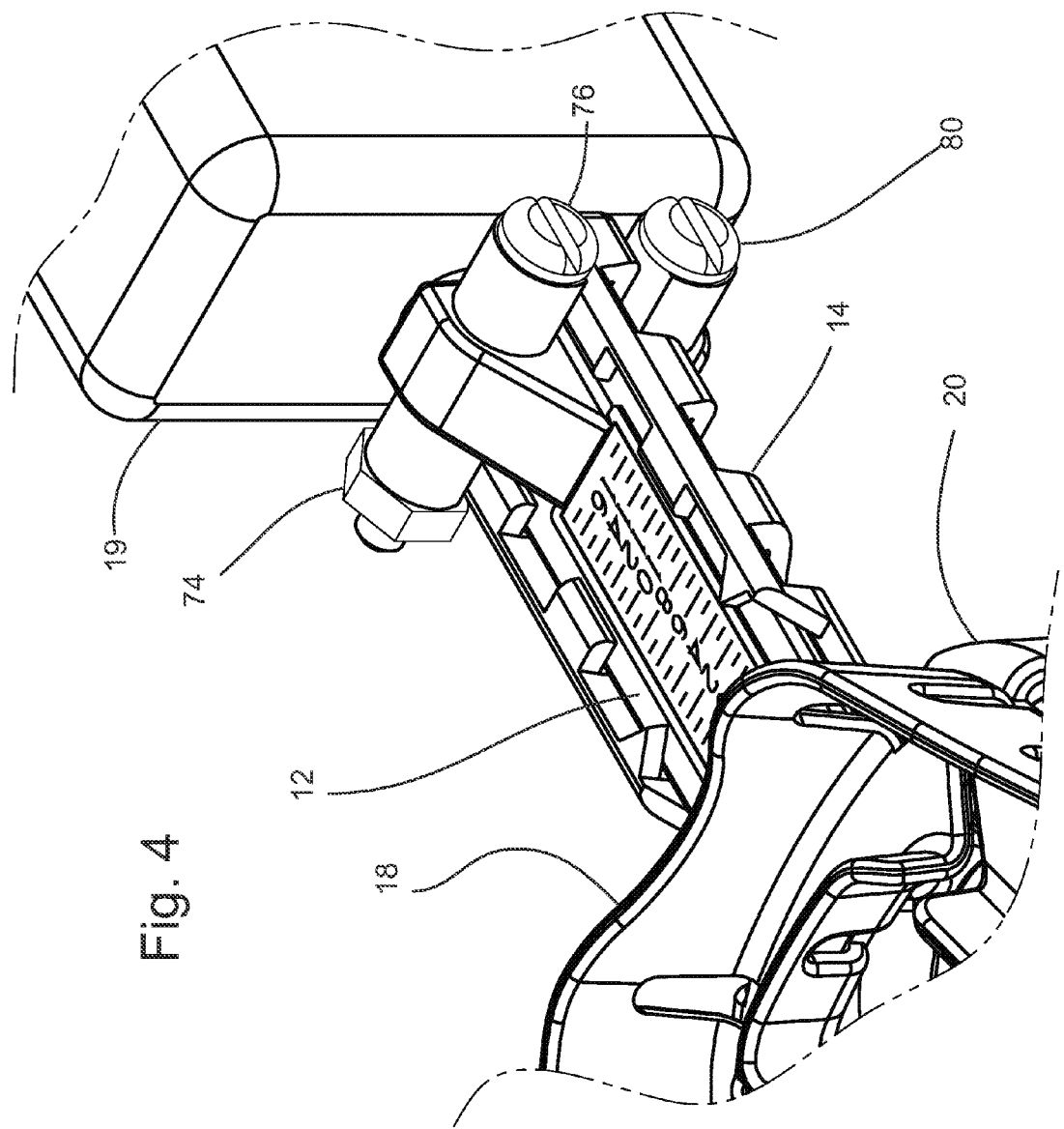

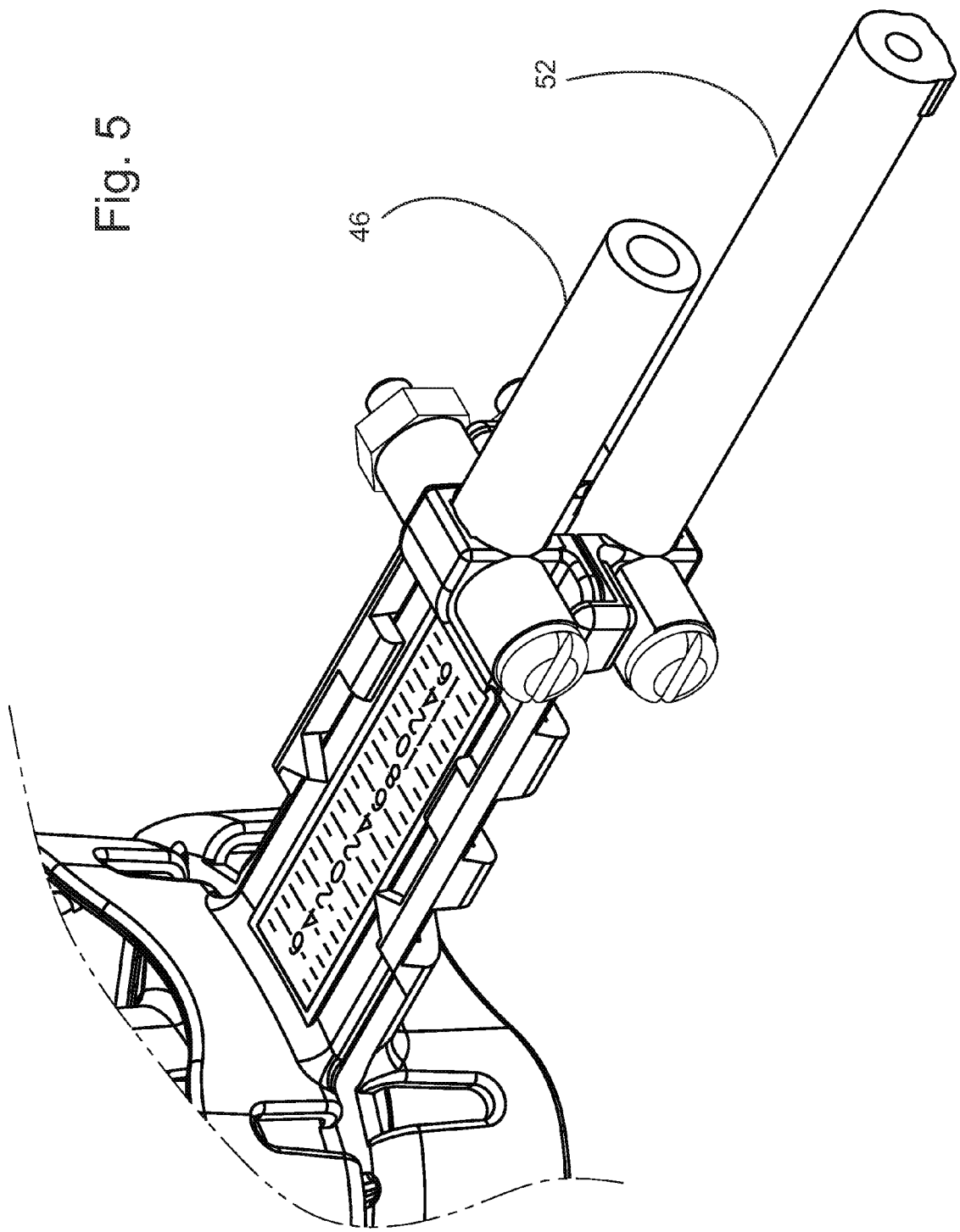

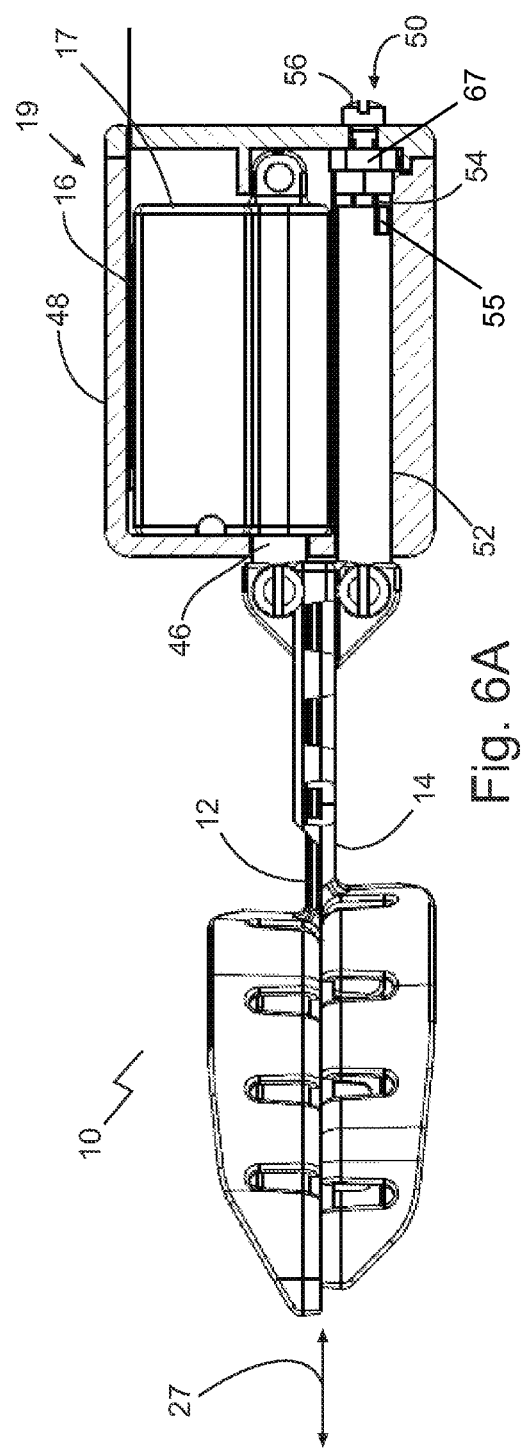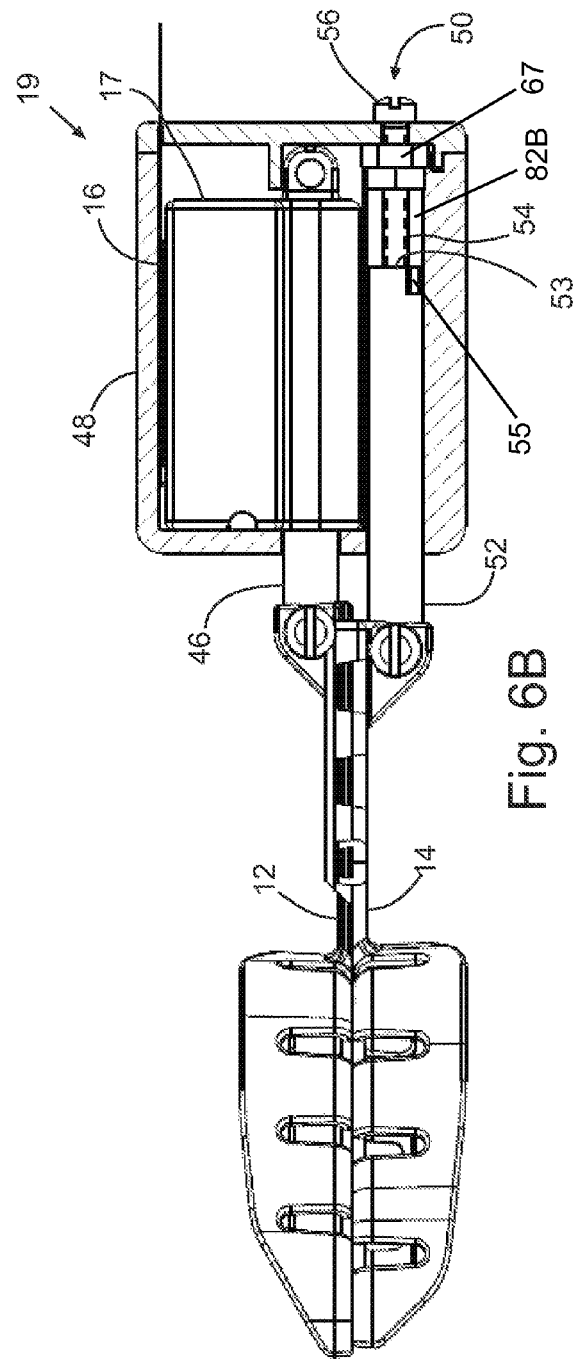

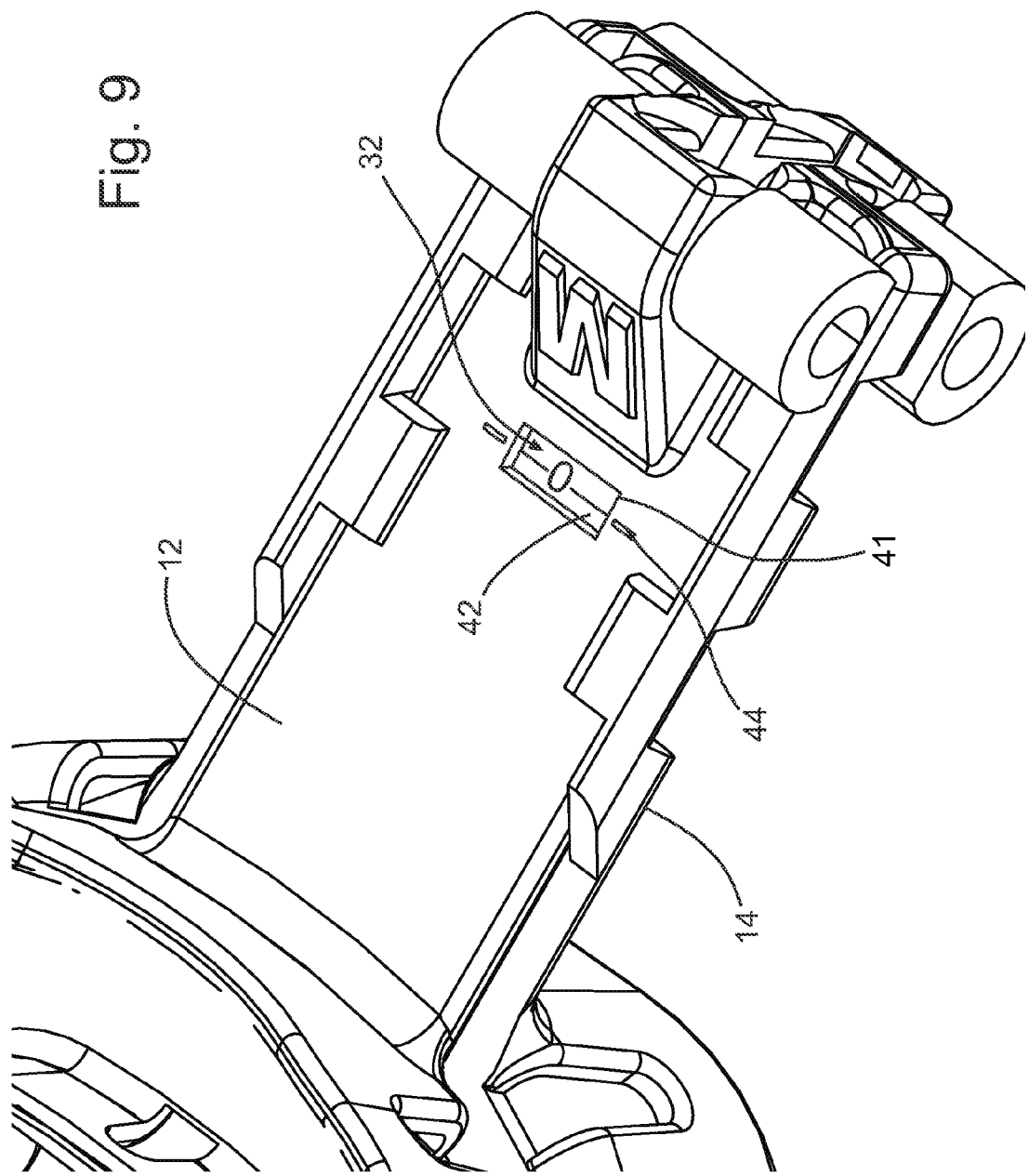

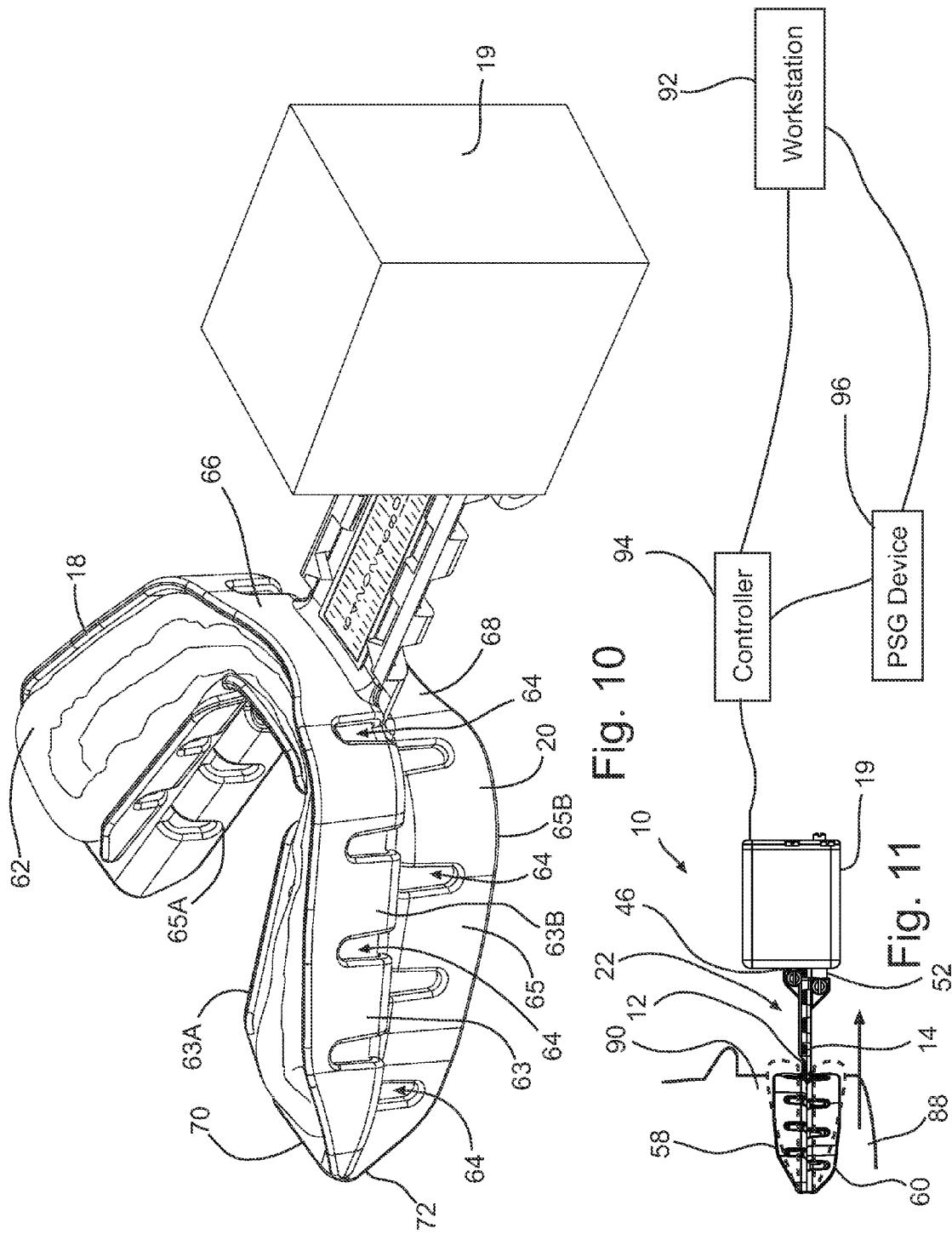

100

Relatively adjusting the position of one of an upper mounting bracket that incorporates an upper dental appliance, and a lower mounting bracket that incorporates a lower dental appliance and is connected to the upper mounting bracket for relative linear movement in the anterior-posterior direction, to an initial position.

102

Relatively displacing the other of the upper mounting bracket and the lower mounting bracket with a drive motor to cause relative displacement between the upper dental appliance and the lower dental appliance to displace the patient's mandible.

Fig. 12

APPARATUSES AND METHODS FOR MANDIBULAR PROTRUSION

RELATED APPLICATIONS

This application claims priority to U.S. Provisional Application No. 61/184,440, filed Jun. 5, 2009, which is incorporated by reference in its entirety.

BACKGROUND

1. Field of the Invention

The present invention relates generally to breathing disorders involving a patient's airway (e.g., snoring, sleep apnea, etc.). More particularly, but not by way of limitation, the present invention relates to apparatuses and methods for mandibular protrusion.

2. Background Information

Obstructive sleep apnea is a relatively common disorder which can produce morbidity and mortality. The disorder arises during sleep when the victim undergoes repeated cessation of breathing. This cessation results from an obstruction of the throat air passage (i.e., pharynx) due to severe narrowing or a collapse of the throat air passage. Repeated cessation of breathing reduces blood oxygen and disturbs sleep. Reduction in blood oxygen can cause hypertension, heart attacks and strokes. Additionally, sleep disturbances can produce excessive daytime sleepiness, headache, depression, irritability and cognitive impairments.

Various apparatus and methods have been proposed for the treatment of sleep disorders, including mandibular protrusion, in which the lower jaw is protruded to relax the pharynx and open the throat air passage.

The following patents include information that may be useful in understanding the present protruders, positioning devices, and methods, and each is incorporated by reference in its entirety: (1) U.S. Pat. No. 5,826,579, issued Oct. 27, 1998; (2) U.S. Pat. No. 5,921,942, issued Jul. 13, 1999; and (3) U.S. Pat. No. 6,273,859, issued Aug. 14, 2001.

SUMMARY

The present disclosure includes embodiments of mandibular protruders, mandibular positioning devices, apparatuses for use with mandibular positioning devices, systems, kits, and methods. Some embodiments of the present mandibular protruders comprise: an upper mounting bracket having an upper dental appliance, a lower mounting bracket having a lower dental appliance; a housing; an actuator (e.g., motor) coupled to and configured to be actuatable to displace one of the upper mounting bracket and lower mounting bracket relative to the housing; and an adjustment mechanism coupled to and configured to be actuated (e.g., manually) to adjust the position of the other of the upper mounting bracket and lower mounting bracket relative to the housing.

Some embodiments of the present mandibular protruders comprise: an upper mounting bracket having an upper dental appliance; a lower mounting bracket having a lower dental appliance; and a rail system configured to couple the upper mounting bracket to the lower mounting bracket. In some embodiments, the rail system is configured to couple the upper mounting bracket to the lower mounting bracket such that relative motion of the lower mounting bracket and the upper mounting bracket is substantially prevented in a lateral direction. In some embodiments, the rail system is configured such that relative motion of the upper mounting bracket to the lower mounting bracket such that relative motion of the lower mounting bracket and the upper mounting bracket is constrained to linear motion in an anterior-posterior direction. In some embodiments, the rail system is spaced apart from the upper dental appliance and the lower dental appliance. In some embodiments, at least one of the upper mounting bracket and the lower mounting bracket includes an elongated planar portion having a length, and the rail system has a length that is less than 70 percent of the length of the elongated planar portion. In some embodiments, the upper mounting bracket, lower mounting bracket, and rail system are configured to be removably coupled to a drive motor. In some embodiments, one of the upper mounting bracket and the lower mounting bracket is configured to be coupled a drive-motor connector of a drive motor, the drive-motor connector having a longitudinal axis that is substantially parallel to the direction of actuation of the drive motor, and the one of the upper mounting bracket and the lower mounting bracket is configured to be coupled to the drive-motor connector such that the longitudinal axis of the one of the upper mounting bracket and the lower mounting bracket is substantially parallel to the longitudinal axis of the drive-motor connector.

Some embodiments further comprise: dental impression material configured to be coupled to at least one of the upper dental appliance and the lower dental appliance, the dental impression material configured to be imprinted with and maintain an impression of a patient's teeth. Some embodiments further comprise: a polymeric bag configured to fit around at least one of the upper dental appliance and the lower dental appliance. In some embodiments, the polymeric bag is configured to fit between the dental impression material and the at least one of the upper dental appliance and lower dental appliance.

In some embodiments, the rail system comprises a portion of one of the lower mounting bracket and the upper mounting bracket that is configured to wrap around a portion of the other of the lower mounting bracket and the upper mounting bracket if the upper mounting bracket is coupled to the lower mounting bracket. In some embodiments, the portion of one of the upper mounting bracket and the lower mounting bracket that is configured to wrap around the other of the upper mounting bracket and the lower mounting bracket is a portion of the lower mounting bracket that is configured to wrap around a portion of the upper mounting bracket. In some embodiments, the portion of the lower mounting bracket that is configured to wrap around the portion of the upper mounting bracket is coupled in fixed relation to the lower mounting bracket, and is configured to slidably engage the upper mounting bracket.

Some embodiments further comprise a relative position indicator configured to indicate relative position of the lower dental appliance to the upper dental appliance if the lower mounting bracket is coupled to the upper mounting bracket. In some embodiments, the relative position indicator is integral with the rail system. In some embodiments, the relative position indicator comprises: a scale coupled to one of the upper mounting bracket and the lower mounting bracket; and an pointer coupled to the other of the upper mounting bracket and the lower mounting bracket; where the relative position indicator is configured such that if the upper mounting bracket is coupled to the lower mounting bracket such that the pointer is within a range of the scale, the pointer will indicate a position of the lower dental appliance relative to the upper dental appliance. In some embodiments, the scale is integral with the upper mounting bracket. In some embodiments, the relative position indicator comprises: a scale coupled to one of the upper mounting bracket and the lower mounting bracket; and a window extending through the other of the upper mounting bracket and the lower mounting bracket; where the relative position indicator is configured such that if the upper mounting bracket is coupled to the lower mounting bracket such that the window is within a range of the scale, the scale is viewable through the window to indicate a position of the lower dental appliance relative to the upper dental appliance. In some embodiments, the scale is integral with the lower mounting bracket. In some embodiments, the relative position indicator further comprises a pointer coupled to the other of the upper mounting bracket and the lower mounting bracket such that if the scale is viewable through the window the pointer will indicate a position of the lower dental appliance relative to the upper dental appliance.

Some embodiments further comprise: a drive motor configured to effect relative displacement of the lower mounting bracket and the upper mounting bracket. Some embodiments further comprise: a plug coupled to the drive motor, and configured to be removably coupled to an external plug to provide a voltage to the drive motor. Some embodiments further comprise: a controller configured to transmit signals to the drive motor to cause the drive motor to effect relative displacement of the lower mounting bracket and the upper mounting bracket. In some embodiments, the controller is configured to sense the relative position of the lower mounting bracket and the upper mounting bracket, and to transmit one or more signals indicative of the position of the lower mounting bracket relative to the upper mounting bracket. In some embodiments, the drive motor is coupled more directly to one of the upper mounting bracket and the lower mounting bracket than to the other of the upper mounting bracket and the lower mounting bracket. In some embodiments, the drive motor is coupled more directly to the upper mounting bracket than to the lower mounting bracket. In some embodiments, the drive motor comprises a linear actuator.

Some embodiments further comprise: a drive motor configured to effect relative displacement of the lower mounting bracket and the upper mounting bracket; and an initial position adjustment mechanism configured to be actuated to adjust the relative position of the lower mounting bracket and the upper mounting bracket independently of the drive motor.

Some embodiments further comprise: a housing coupled to the drive motor and the initial position adjustment mechanism; where the drive motor is configured to adjust the position of one of the upper mounting bracket and the lower mounting bracket relative to the housing (e.g., to adjust the relative position of the lower mounting bracket and the upper mounting bracket); and where the initial position adjustment mechanism is configured to be actuated to adjust the position of other of the upper mounting bracket and the lower mounting bracket relative to the housing (e.g., to adjust the relative position of the lower mounting bracket and the upper mounting bracket).

In some embodiments, the upper dental appliance comprises an upper dental tray, and the lower dental appliance comprises a lower dental tray. In some embodiments, at least one of the upper dental tray and the lower dental tray includes a front portion and two lateral portions, and is configured to permit the lateral portions to flex relative to the front portion. In some embodiments, the upper dental appliance is integral with the upper mounting bracket, and the lower dental appliance is integral with the lower mounting bracket. In some embodiments, the upper mounting bracket is configured to be coupled to a connector of an initial adjustment mechanism or a drive motor, and the lower mounting bracket is configured to be coupled to a connector of an initial adjustment mechanism or a drive motor. In some embodiments, the upper mounting bracket has a longitudinal axis and a recess configured to receive a portion of the connector, the recess having an outer portion with a first cross-section, an inner portion having a second cross-section that is different than the first cross-section, and an opening extending transverse to the longitudinal axis of the upper mounting bracket, and through the upper mounting bracket across the inner portion of the recess; and the lower mounting bracket has a longitudinal axis and a recess configured to receive a portion of the connector, the recess having an outer portion with a first cross-section, an inner portion having a second cross-section that is different than the first cross-section, and an opening extending transverse to the longitudinal axis of the lower mounting bracket, and through the lower mounting bracket across the inner portion of the recess.

Some embodiments of the present apparatuses and/or mandibular protruders comprise: an upper mounting bracket having an upper dental tray; and a lower mounting bracket having a lower dental tray; where at least one of the upper dental tray and the lower dental tray includes a front portion and two lateral portions, and is configured to permit the lateral portions to flex relative to the front portion.

Some embodiments of the present mandibular positioning devices comprise: a drive motor having a connector configured to be coupled to a mounting bracket of a first dental appliance; an adjustment mechanism having a connector configured to be coupled to a mounting bracket of a second dental appliance; and a housing having a sidewall with at least a first opening and a second opening, the housing coupled to the drive motor and the adjustment mechanism such that the housing encloses at least a portion of each of the drive motor and the adjustment mechanism, the drive-motor connector extends out of the housing through the first opening, and the adjustment-mechanism connector extends out of the housing through the second opening; where the adjustment mechanism is configured to linearly adjust the position of the adjustment-mechanism connector; and where the drive motor is configured to linearly move the drive-motor connector in a direction substantially parallel to the direction in which the adjustment mechanism can adjust the adjustment-mechanism connector.

Some embodiments further comprise: a first seal disposed around the drive-motor connector between the housing and the drive-motor connector; and a second seal disposed around the adjustment-mechanism connector between the housing and the adjustment-mechanism connector. In some embodiments, the first seal and the second seal each comprises a seal body and a coil spring coupled to the seal body.

In some embodiments, the adjustment-mechanism connector includes a longitudinal axis, a proximal portion having a first cross-section, and a distal portion having a second cross-section that is different than the first cross-section; and the drive-motor connector includes a longitudinal axis, a proximal portion having a first cross-section, and a distal portion having a second cross-section that is different than the first cross-section. In some embodiments, the adjustment-mechanism connector includes a hole extending through the distal portion of the adjustment-mechanism connector transverse to the longitudinal axis; and the drive-motor connector includes a hole extending through the distal portion of the drive-motor connector transverse to the longitudinal axis.

Some embodiments of the present mandibular protruders comprise: an upper mounting bracket having an upper dental appliance; a lower mounting bracket having a lower dental appliance, the lower mounting bracket configured to be coupled to the upper mounting bracket such that relative motion of the lower mounting bracket and the upper mounting bracket is constrained to linear motion in an anterior-posterior direction; a mandibular positioning device configured to be coupled to the upper mounting bracket and the lower mounting bracket, the mandibular positioning device having a drive motor configured to adjust the relative position of the lower mounting bracket and the upper mounting bracket if the mandibular positioning device is coupled to the upper mounting bracket and the lower mounting bracket; an upper release mechanism configured to release the upper dental appliance from the mandibular positioning device if the mandibular positioning device is coupled to the upper mounting bracket; and a lower release mechanism configured to release the lower dental appliance from the mandibular positioning device if the mandibular positioning device is coupled to the lower mounting bracket.

Some embodiments of the present mandibular protruders comprise: an upper mounting bracket having an upper dental appliance; a lower mounting bracket having a lower dental appliance, the lower mounting bracket configured to be coupled to the upper mounting bracket such that the lower mounting bracket can move linearly relative to the upper mounting bracket; a drive motor coupled to one of the upper mounting bracket and the lower mounting bracket, the drive motor configured to effect relative displacement of the lower mounting bracket and upper mounting bracket; and an initial position adjustment mechanism configured to adjust an initial position of the other of the upper mounting bracket and the lower mounting bracket. In some embodiments, the initial position adjustment mechanism comprises a manually operable element. In some embodiments, the initial position adjustment mechanism comprises a screw.

Some embodiments of the present mandibular protruders comprise: an upper mounting bracket having an upper dental appliance; a lower mounting bracket having a lower dental appliance, the lower mounting bracket configured to couple the upper mounting bracket to the lower mounting bracket such that relative motion of the lower mounting bracket and the upper mounting bracket is constrained to linear motion in an anterior-posterior direction; a drive motor coupled more directly to one of the upper mounting bracket and the lower mounting bracket than to the other of the upper mounting bracket and the lower mounting bracket, the drive motor configured to effect relative displacement of the lower mounting bracket and the upper mounting bracket. In some embodiments, the drive motor comprises a linear actuator configured to effect relative displacement of the lower mounting bracket and the upper mounting bracket in the anterior-posterior direction. Some embodiments further comprise: an initial position adjustment mechanism having a connector coupled to the other of the upper mounting bracket and the lower mounting bracket, the initial position adjustment mechanism configured to be actuated to adjust relative position of the lower mounting bracket and the upper mounting bracket independently of the drive motor.

Some embodiments of the present apparatuses for use with a mandibular positioning device, comprise: an upper mounting bracket having an upper dental appliance; a lower mounting bracket having a lower dental appliance, the lower mounting bracket configured to be coupled to the upper mounting bracket such that relative linear motion of the lower mounting bracket and the upper mounting bracket is permitted; and a relative position indicator for indicating relative position of the lower dental appliance and the upper dental appliance; where the apparatus is configured such that the lower mounting bracket can be coupled to the upper mounting bracket and such that the upper mounting bracket and the lower mounting bracket can be independently coupled to a first connector and a second connector respectively of a mandibular positioning device. In some embodiments, the relative position indicator comprises quantitative elements. Some embodiments further comprise a drive motor configured to effect relative displacement of the lower mounting bracket and the upper mounting bracket.

Some embodiments of the present methods comprise: adjusting the relative position of one of an upper mounting bracket having an upper dental appliance, and a lower mounting bracket having a lower dental appliance, the lower mounting bracket coupled to the upper mounting bracket such that relative motion of the lower mounting bracket and the upper mounting bracket is constrained to linear motion in an anterior-posterior direction; and relatively displacing with a drive motor the other of the upper mounting bracket and the lower mounting bracket when a patient's upper teeth are disposed in the upper dental appliance and the patient's lower teeth are disposed in the lower dental appliance to cause relative displacement of the upper dental appliance and the lower dental appliance and displace the patient's mandible relative to the patient's maxilla.

In some embodiments, relatively displacing the other of the upper mounting bracket and the lower mounting bracket protrudes the patient's mandible relative to the patient's maxilla. In some embodiments, relatively displacing is repeated while the patient's breathing is monitored. In some embodiments, relatively displacing is performed responsive to detection of an interruption in the patient's breathing. Some embodiments further comprise: determining an optimal mandibular displacement for the patient at which the patient experiences less than a predetermined maximum number of respiratory disturbances in a period of time. In some embodiments, the maximum number of respiratory disturbances corresponds to a respiratory disturbance index (RDI). In some embodiments, the predetermined maximum number of respiratory disturbances corresponds to an RDI of 10 per hour. In some embodiments, the predetermined number of respiratory disturbances corresponds to no snoring and/or no inspiratory flow limitation (e.g., during rapid eye movement (REM) sleep) and/or is measured when the patient is supine). In some embodiments, the predetermined maximum number of respiratory disturbances corresponds to an RDI that is less than a baseline RDI for the patient. In some embodiments, the period of time is 10 minutes. In some embodiments, the optimal mandibular protrusion is determined from a relative position indicator that indicates relative position of the lower dental appliance and the upper dental appliance. Some embodiments further comprise: communicating the optimal mandibular displacement for the patient to an entity (e.g., a dentist) for construction of a mandibular protrusion oral appliance for the patient. Some embodiments further comprise: adjusting an oral appliance to cause a mandibular displacement if worn by the patient corresponding to the optimal mandibular displacement.

Some embodiments of the present methods comprise: providing an embodiment of the present mandibular protruders (e.g., a protruder comprising: an upper mounting bracket having an upper dental appliance; a lower mounting bracket having a lower dental appliance; a rail system coupling the upper mounting bracket to the lower mounting bracket; a drive motor configured to effect relative displacement of the lower mounting bracket and the upper mounting bracket; and an initial position adjustment mechanism configured to be actuated to adjust the relative position of the lower mounting bracket and the upper mounting bracket independently of the drive motor); actuating the initial position adjustment mechanism to adjust the relative position of the upper mounting bracket and the lower mounting bracket; and relatively displacing with the drive motor the upper mounting bracket and the lower mounting bracket when a patient's upper teeth are coupled to the upper dental appliance and the patient's lower teeth are coupled to the lower dental appliance to cause relative displacement between the upper dental appliance and the lower dental appliance and displace the patient's mandible relative to the patient's maxilla.

Some embodiments further comprise: monitoring one or more characteristics of the patient while the patient sleeps; where relatively displacing is performed responsive to the one or more characteristics to reduce the one or more characteristics. Some embodiments further comprise: determining an optimal mandibular displacement for the patient at which at least one of the one or more characteristics is minimized. Some embodiments further comprise: adjusting an oral appliance to cause a mandibular displacement if worn by the patient that corresponds to the optimal mandibular displacement.

Some embodiments of the present methods comprise: disposing a mandibular positioning device in a polymeric bag such that a drive-motor connector of the mandibular positioning device and an adjustment-mechanism connector of the mandibular positioning device extend out of the polymeric bag; and coupling an upper mounting bracket having an upper dental appliance to one of the drive-motor connector and the adjustment-mechanism connector, and a lower mounting bracket having a lower dental appliance to the other of the drive-motor connector and the adjustment-mechanism connector. In some embodiments, the upper mounting bracket and the lower mounting bracket are coupled to the connectors such that the upper mounting bracket and lower mounting bracket are coupled to each other by a rail system. Some embodiments further comprise: actuating the device to displace a patient's mandible relative to the patient's maxilla.

Some embodiments of the present oral appliances comprise: an oral appliance that has been adjusted to cause an optimal mandibular displacement if worn by a patient, the optimal mandibular displacement for the patient having been determined by a sleep titration performed with a mandibular protruder (e.g., a mandibular protruder comprising: an upper mounting bracket having an upper dental appliance; a lower mounting bracket having a lower dental appliance; and a rail system configured to couple the upper mounting bracket to the lower mounting bracket).

Some embodiments of the present systems comprise: any embodiment of the present mandibular protruders, any embodiment of the present mandibular positioning devices, and/or any embodiments of the present apparatuses for use with the mandibular protruders; a computer program product comprising tangible computer-readable media (e.g., a disk, thumb drive, flash drive, hard drive, etc.) having computer-executable instructions for performing any of the present methods; and/or a computer configured to execute the computer-readable instructions.

A mandibular protruder is disclosed, comprising: an upper mounting bracket; a lower mounting bracket secured to the upper mounting bracket by a rail system constraining relative motion of the lower mounting bracket and the upper mounting bracket to linear motion in the anterior-posterior direction; the upper mounting bracket incorporating an upper dental appliance; and the lower mounting bracket incorporating a lower dental appliance. In some embodiments of the mandibular protruders disclosed herein, the upper dental appliance is integral with, for example molded as a part of, the upper mounting bracket. Similarly, in some embodiments the lower dental appliance is integral with, for example molded as a part of, the lower mounting bracket.

A mandibular protruder is also disclosed, comprising: an upper dental appliance connected to a mandibular positioning device through an upper mounting bracket; a lower dental appliance connected to the mandibular positioning device through a lower mounting bracket, the lower mounting bracket being connected to the upper mounting bracket for relative linear movement; the mandibular positioning device having a drive motor for effecting relative displacement of the lower mounting bracket and the upper mounting bracket; the mandibular protruder incorporating an upper release mechanism, such as an upper connector, for release of the upper dental appliance from the mandibular positioning device; and the mandibular protruder incorporating a lower release mechanism, such as a lower connector, for release of the lower dental appliance from the mandibular positioning device.

A mandibular protruder is also disclosed, comprising: an upper mounting bracket; a lower mounting bracket connected to the upper mounting bracket for relative linear movement; a drive motor for effecting relative displacement of the lower mounting bracket and the upper mounting bracket; the drive motor being connected to one of the upper mounting bracket and the lower mounting bracket; an initial position adjustment mechanism limiting an initial position of the other of the upper mounting bracket and the lower mounting bracket; the upper mounting bracket incorporating an upper dental appliance; and the lower mounting bracket incorporating a lower dental appliance.

A mandibular protruder is also disclosed, comprising: an upper mounting bracket; a lower mounting bracket connected to the upper mounting bracket for relative linear movement; a drive motor for effecting relative displacement of the lower mounting bracket and the upper mounting bracket; the upper mounting bracket incorporating an upper dental appliance; the lower mounting bracket incorporating a lower dental appliance; and a relative position indicator for indicating relative position of the lower dental appliance to the upper dental appliance.

A method is also disclosed of displacing a patient's mandible relative to the patient's maxilla, the method comprising: relatively adjusting the position of one of an upper mounting bracket that incorporates an upper dental appliance, and a lower mounting bracket that incorporates a lower dental appliance and is connected to the upper mounting bracket for relative linear movement in the anterior-posterior direction, to an initial position; and relatively displacing the other of the upper mounting bracket and the lower mounting bracket with a drive motor to cause relative displacement between the upper dental appliance and the lower dental appliance to displace the patient's mandible.

A mandibular protruder is also disclosed, comprising: an upper mounting bracket; a lower mounting bracket secured to the upper mounting bracket by a connection system allowing at least relative motion of the lower mounting bracket and the upper mounting bracket in the anterior-posterior direction; the upper mounting bracket incorporating an upper dental appliance; the lower mounting bracket incorporating a lower dental appliance; and a drive motor for effecting relative displacement of the lower mounting bracket and the upper mounting bracket, the drive motor being connected to drive one of the upper mounting bracket and the lower mounting bracket, the drive motor comprising a linear actuator.

A mandibular protruder is also disclosed, comprising: an upper mounting bracket; a lower mounting bracket secured to the upper mounting bracket by a connection system allowing at least relative motion of the lower mounting bracket and the upper mounting bracket in the anterior-posterior direction;

the upper mounting bracket incorporating an upper dental appliance; the lower mounting bracket incorporating a lower dental appliance; a drive motor for effecting relative displacement of the lower mounting bracket and the upper mounting bracket, the drive motor being connected to drive one of the upper mounting bracket and the lower mounting bracket; and an initial position adjustment mechanism connected to the other of the upper mounting bracket and the lower mounting bracket through a connector.

In some embodiments, the mandibular protruders disclosed herein are devices used to measure suitability and optimal jaw displacement (e.g., optimal mandibular protrusion).

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

In FIG. 1A, upper and lower dental trays of the protruder are in a fully retracted position, in FIG. 1B the upper dental tray is extended and the lower dental tray is in the fully retracted position, and in FIG. 1C the upper dental tray is retracted and the lower dental tray is at least partially extended from the retracted position of FIG. 1A.

FIG. 2 is a side elevation view of the mandibular protruder of FIG. 1A with the dental trays retracted to the zero point on the scale.

FIG. 2A is a perspective view of a mandibular positioning device suitable for use in the mandibular protruder of FIG. 1A.

FIG. 4 is a perspective view of the rail system of the mandibular protruder of FIG. 1A.

FIG. 5 is a further perspective view of the rail system of a mandibular protruder of FIG. 1A shown without a portion of the mandibular positioning device.

FIGS. 6A and 6B are partially cutaway, side elevation views of the mandibular protruder of FIG. 1A showing the lower dental tray in fully retracted and offset positions, respectively.

FIG. 9 is a perspective view of another embodiment of a relative position indicator that incorporates a reference window for a displacement scale, and that is suitable for use in embodiments of the present mandibular protruders.

FIG. 10 is a perspective view of one of the present mandibular protruders shown with bite material, shaped to fit a user's teeth, fitted in the upper and lower dental trays.

FIG. 11 is a schematic illustrating an exemplary system for carrying out a sleep titration on a patient with a mandibular protruder.

FIG. 12 is a flow diagram of one of the present methods of displacing a patient's mandible relative to the patient's maxilla.

DESCRIPTION OF ILLUSTRATIVE EMBODIMENTS

Figure 1A:
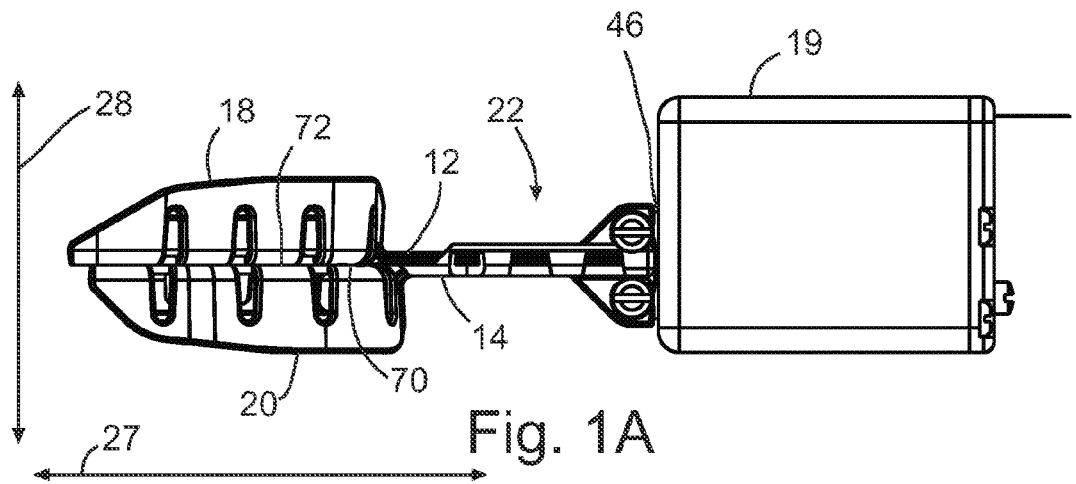
FIGS. 1A-1C are side elevation views of one of the present mandibular protruders.

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. For example, in a method that comprises adjusting the initial relative position of a lower dental appliance and an upper dental appliance, and relatively displacing the lower dental appliance and the upper dental appliance: the method includes the specified steps but is not limited to having only those steps. For example, such a method could also include determining an optimal mandibular displacement for a patient. Likewise, an apparatus that "comprises," "has," "includes" or "contains" one or more elements possesses those one or more elements, but is not limited to possessing only those elements. For example, in a mandibular protruder that comprises an upper dental appliance and a lower dental appliance, the mandibular protruder includes the specified elements but is not limited to having only those elements (e.g., such a protruder could also have a drive motor).

Further, a device or structure that is configured in a certain way is configured in at least that way, but it can also be configured in other ways than those specifically described.

Referring to FIGS. 1-6B and 7, one embodiment is shown of the present mandibular protruders 10 that comprises an upper mounting bracket 12, and a lower mounting bracket 14. Upper mounting bracket 12 may incorporate an upper dental appliance 18, and lower mounting bracket 12 may incorporate a lower dental appliance 20. For example, in the embodiment shown upper mounting bracket 12 has an upper dental appliance 18 that includes a dental tray, and lower mounting bracket 14 has a lower dental appliance 20 that includes a lower dental tray. In the embodiment shown, upper mounting bracket 12 includes an elongated planar portion that extends from a first end coupled to upper dental appliance 18 to a second end that is configured to be coupled to (and is shown coupled) to device 19 (e.g., via connector 46); and lower mounting bracket 14 has an elongated planar portion that extends from a first end coupled to lower dental appliance 20 to a second end that is configured to be coupled to (and is shown coupled) to device 19 (e.g., via connector 50).

Figure 3A:
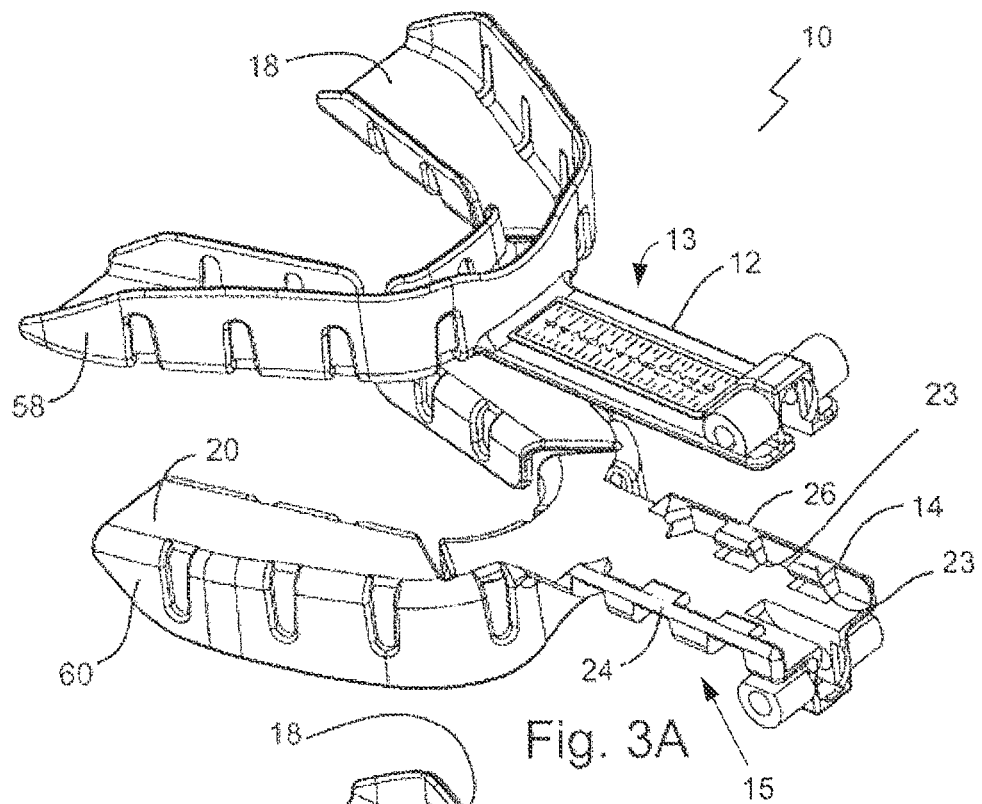
FIGS. 3A and 3B are perspective views of the upper and lower dental trays suitable for use in the mandibular protruder of FIG. 1A.
Figure 3B:
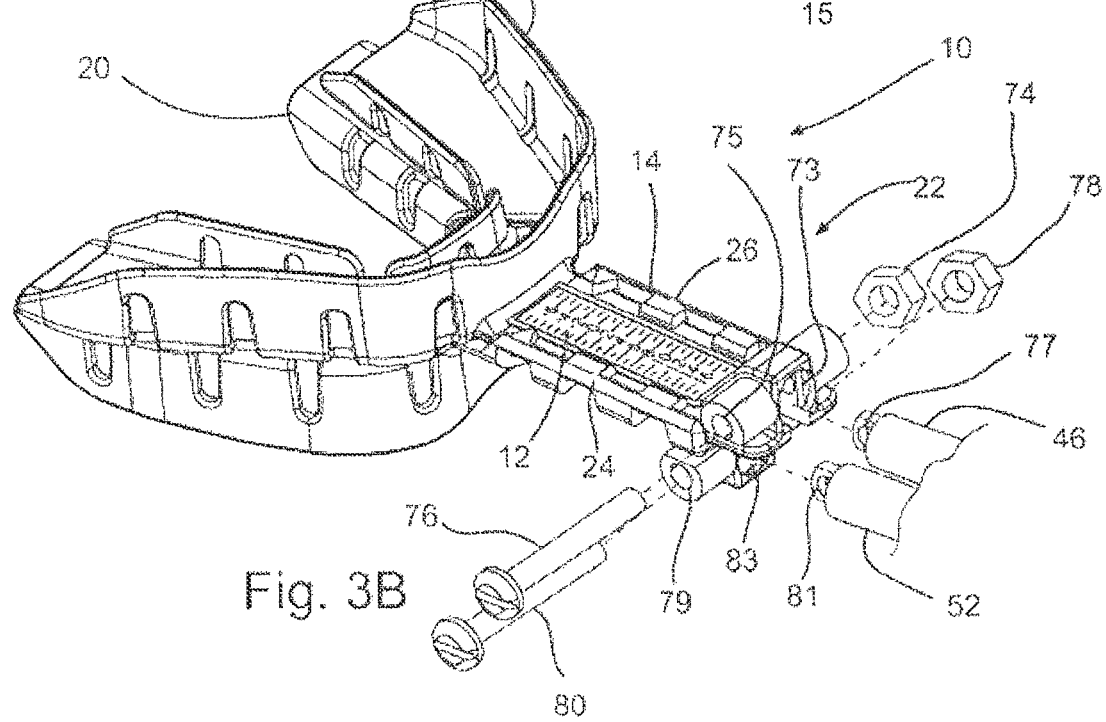

As shown, for example, in FIGS. 3A-3B, lower mounting bracket 14 may be secured to upper mounting bracket 12 by a connection system that allows at least relative motion of lower mounting bracket 14 and upper mounting bracket 12 in an anterior-posterior direction 27. Anterior-posterior direction generally refers to the direction that extends between a user's anterior (e.g., chin) and a user's posterior (e.g., spine). In some embodiments, lower mounting bracket 14 may be connected to upper mounting bracket 12 for relative linear movement. For example, brackets 12 and 14 may be secured and/or coupled to one another by a connection system 22, (e.g., in the embodiment shown, a rail system 22) that is configured to couple upper mounting bracket 12 to lower mounting bracket 14. In some embodiments, rail system 22 is configured to couple upper mounting bracket 12 to lower mounting bracket 14 such that relative motion of lower mounting bracket 14 and upper mounting bracket 12 is substantially prevented in a lateral direction (e.g., by sides 24 and 26). In the embodiment shown, rail system 22 is configured to constrain relative motion of lower mounting bracket 14 and upper mounting bracket 12 to linear motion in the anterior-posterior direction (indicated by arrows 27 in FIG. 1A). For example, in the embodiment shown, protruder 10 comprises a rail system 22 that is configured to couple upper mounting bracket 12 to lower mounting bracket 14 such that relative motion of the lower mounting bracket and the upper mounting bracket is constrained to linear motion in anterior-posterior direction 27.

In the embodiment shown, rail system 22 comprises portions of one or both of upper and lower mounting brackets 12 and 14, respectively, and/or may otherwise be configured act as a slide guidance mechanism (e.g., to allows accurate anterior/posterior (A-P) positioning of the upper dental appliance 18 with respect to the lower dental appliance 20). In the embodiment shown, rail system 22 is configured such that if upper mounting bracket 12 is coupled to lower mounting bracket 12, relative motion of upper mounting bracket 12 and lower mounting bracket is constrained to linear motion in the A-P direction (e.g., such that rail system 22 prevents vertical and lateral relative movement of the mounts 12 and 14 and thereby appliances 18 and 20). In some embodiments, rail system 22 can be configured to provide or permit telescopic movement. Rail system 22 may comprise a portion of one of lower mounting bracket 14 and the upper mounting bracket 12 configured to wrap and/or wrapping at least partially around a portion of the other of lower mounting bracket 14 and upper mounting bracket 12 if upper mounting bracket 12 is coupled to lower mounting bracket 14, as shown in FIGS. 3A-3B. For example, in the embodiment shown, a portion of lower mounting bracket 14 is configured to wrap around a portion of upper mounting bracket 12 (e.g., such that the portion of lower mounting bracket 14 that is configured to wrap around the portion of upper mounting bracket 12 is coupled in fixed relation to lower mounting bracket 14, and is configured to slidably engage upper mounting bracket 14).

For example, in the embodiment shown in FIGS. 3A and 3B, lower mounting bracket 14 includes wrap-around edges 24 and 26 along a subsection of the length of lower mounting bracket 14 that are configured to wrap around upper mounting bracket 12 such that upper mounting bracket 12 can slide relative to lower mounting bracket 14 between edges 24 and 26, if lower mounting bracket 14 is coupled to upper mounting bracket 12. For example, in the embodiment shown, edges 24 and 26 are configured to provide a channel in which lower mounting bracket 12 can slide relative to lower mounting bracket 14. Edges 24 and 26 may include and/or be partially defined by guides 23 (e.g., a plurality of guides that extend from sides 24 and 26 over the top of upper mounting bracket 12 when upper and lower mounting brackets 12 and 14 are coupled or assembled), which may, for example, be extensions of the respective bracket 12 or 14. In the embodiment shown, a plurality of guides 23 extend from each of sides 24 and 26. For example, at least two guides 23 on at least one of (e.g., both of) sides 24 and 26 are spaced apart to discourage (e.g., independently of a drive motor or adjustment mechanism) vertical rotation of upper mounting bracket 12 relative to lower mounting bracket 14. Similarly, sides 24 and 26 each extends between two spaced-apart points (e.g., has a length) to discourage (e.g., independently of a drive motor or adjustment mechanism) horizontal rotation of upper mounting bracket 12 relative to lower mounting bracket 14. As illustrated, for example, in FIGS. 1A, 3B, and 7, rail system 22 is configured to act as a captive enclosure that aligns upper and lower mounting brackets 12 and 14 (and thereby dental appliances 18 and 20), and prevents relative movement of the brackets in a coronal dimension (indicated by arrows 28 in FIG. 1A), and, in the embodiment shown, prevents relative movement of the brackets in a lateral dimension (indicated by arrows 30 in FIG. 7), thereby allowing relative motion of the mounting brackets 12, 14 only in the A-P dimension or direction 27.

A-P dimension or direction 27 generally refers to a dimension or direction that extends from the incisors posteriorly in the occlusal plane (e.g., when protruder is coupled to a patient for use, as described below). A-P direction is not absolute, and instead corresponds to the longitudinal axis of upper mounting bracket 12 and/or the longitudinal axis 14 of lower mounting bracket 14 (which are parallel in the embodiment shown). Lateral dimension or direction 30 generally refers to an axis perpendicular (at a right angle to) A-P dimension 27 and that is also in the occlusal plane. The vertical (or Coronal) dimension or direction 28 refers to an axis that is at right angles to the A-P and lateral directions, in the cranial-caudal direction and parallel to the separation between the occlusal planes. (and may be typically conceived of as passing through the incisors). The dimensions or directions 27, 28, and 30 correlate to when mandibular protruder 10 is positioned in a user's mouth (not shown) and, as noted above, can be related to the longitudinal axes of upper and lower mounting brackets 12 and 14, respectively, for the embodiment shown of protruder 10.

Rail system 22 may, in some embodiments, be configured to completely restrict lateral motion by reducing the tolerance between brackets 12 and 14 (e.g., configuring brackets 12 and 14 to fit together more or very closely, such as, for example, via rail system 22). In other embodiments, rail system 22 can be configured to allow some lateral relative motion of or between upper mounting bracket 12 and lower mounting bracket 14 by increasing the tolerance between brackets 12 and 14 (e.g., configuring brackets 12 and 14 to fit together more or very closely, such as, for example, via rail system 22). In some embodiments, increased lateral motion may also be afforded by pairing upper mounting bracket 12 and/or lower mounting bracket 14 (e.g., rail system 22) with a connector (not shown) that is configured to permit some rotation around coronal dimension or direction 28. In the embodiment shown, the upper side of lower mounting bracket 14 faces and the lower side of upper mounting bracket 12 such that that they can slide in relation to each other in the anterior-posterior (A-P) dimension 27.

In some embodiments, at least one of brackets 12 and 14 may be flexible to accommodate assembly of rail system 22. For example, upper mounting bracket 12 may be configured to be flexible such that upper mounting bracket 12 can be compressed perpendicular to A-P direction 27 to reduce its width in direction 30 such that upper mounting bracket 12 can be placed between sides 24 and 26 of lower mounting bracket 14, and the compression released such that upper mounting bracket 12 returns to its original shape and extends under guides 23 of lower mounting bracket 14. Alternatively, upper and lower mounting brackets 12 and 14 can be coupled or assembled by sliding upper mounting bracket 12 from anterior to posterior in A-P direction 27 such that upper mounting bracket 14 extends between sides 24 and 26 and under guides 23. In some embodiments, increased vertical relative motion can be permitted between upper mounting bracket 12 and lower mounting bracket 14, such as, for example, by increasing the tolerances therebetween (e.g., between guides 23 and upper mounting bracket 12), omitting guides 23 such that the rail system includes sides 24 and 26 to restrict or constrain lateral movement but does not include guides 23 to restrict or constrain vertical relative movement, and/or the like. In some embodiments, the rail system can comprise, for example, a single rail (e.g., a single vertical member similar to side 24 or 26) extends from the middle of lower mounting bracket 14, through a slot in upper mounting bracket 12, and/or having a guide (e.g., 23) extending laterally to one or both sides of the slot, such that the rail system is configured to constrain lateral and/or vertical relative motion of upper mounting bracket 12 and lower mounting bracket 14.

In some embodiments, protruder 10 comprises a relative position indicator, such as scale 32 and pointer 34, for indicating (configured to indicate) relative position of upper mounting bracket 12 and lower mounting bracket 14 (and/or lower dental appliance 20 and upper dental appliance 18) if lower mounting bracket 14 is coupled to upper mounting bracket 12. As used in this disclosure, relative motion and relative position of upper mounting bracket 12 (and upper dental appliance 18) and lower mounting bracket 14 (and lower dental appliance 20) generally refers to motion or position of lower mounting bracket 14 relative to upper mounting bracket 12 (and/or vice versa). In the embodiment shown, at least a portion of the relative position indicator is integral with rail system 22 (e.g., pointers 34 are integral with sides 24 and 26 and configured to function similarly to guides 23). More particularly, in the embodiment shown in FIG. 7, the relative position indicator comprises: scale 32 coupled to upper mounting bracket; and at least one pointer 34 (e.g., two pointers 34) coupled to lower mounting bracket 12. In this embodiment, the relative position indicator (e.g., pointer 34 and scale 32) is configured such that if upper mounting bracket 12 is coupled to lower mounting bracket 14 such that pointer 34 is within a range of scale 32, pointer 34 will indicate a position of lower dental appliance 14 relative to upper dental appliance 12 (e.g., a relative position therebetween). In some embodiments, scale 32 is integral with upper mounting bracket 12. In some embodiments, scale 32 comprises a GEORGE GAUGE scale.

Figure 7:
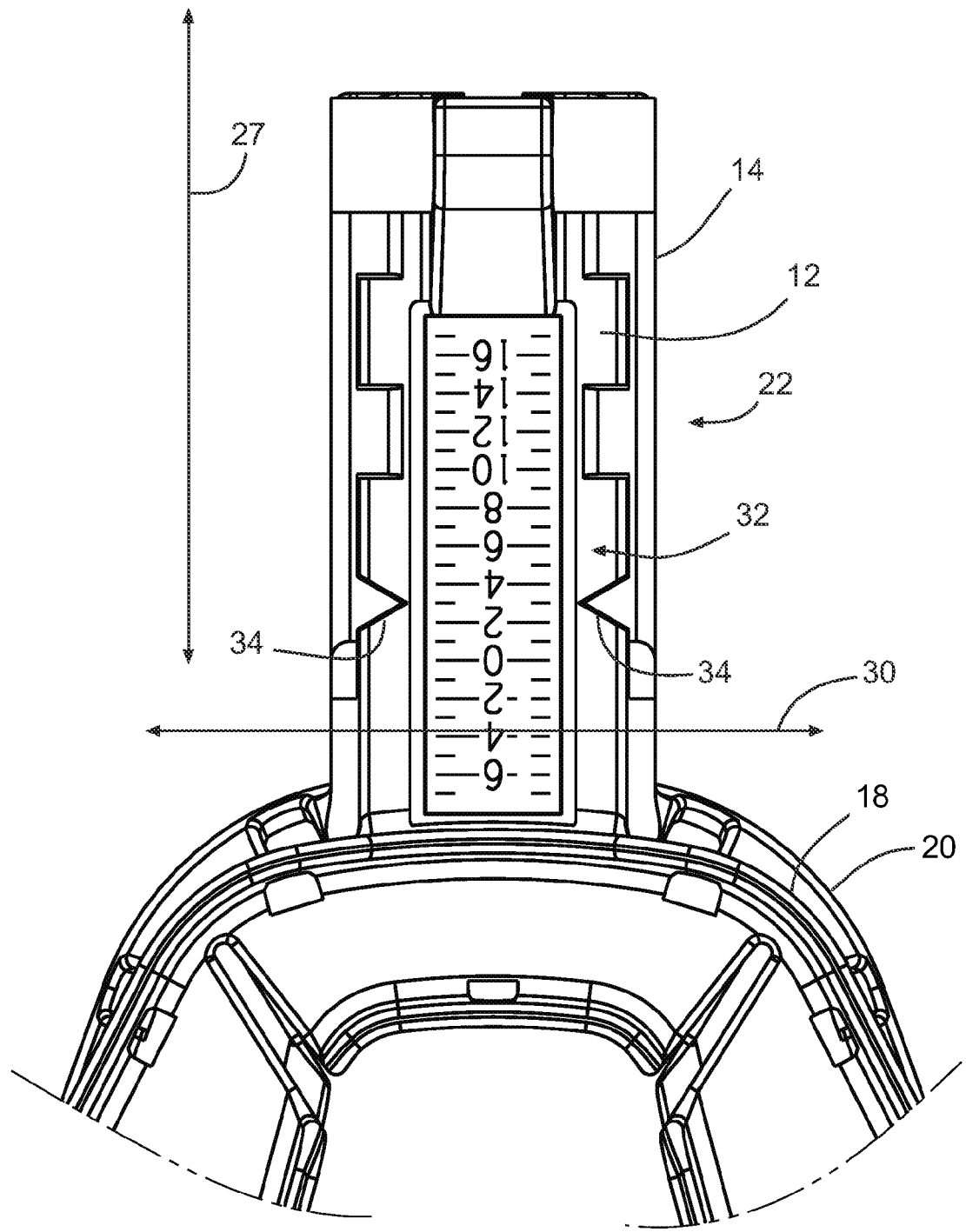
FIG. 7 is a top plan view of a relative position indicator of the mandibular protruder of FIG. 1A, that includes a displacement scale.

The relative position indicator may be at least partially formed of parts, such as pointer 34, of the rail system 22. The relative position indicator may comprise quantitative elements, such as the markings that make up (are included in) scale 32. The relative position indicator allows the relative displacement between appliances 18 and 20 to be accurately measured by measuring the relative displacement between upper and lower mounting brackets 12 and 14. Pointer 34 may be an arrow-shaped guide, as shown in FIG. 7.

In the embodiment illustrated, mounting brackets 12 and 14 cooperate to display a graduated measuring system, located for example on the struts (elongated portions) of brackets 12 and 14, that allows a physician or other user to measure the relative position of appliances 18 and 20 (for or unique to a patient) during a fitting or other procedure for the patient. Scale 32 may provide a reference value of retrusion of the lower jaw, for example indicative of a point where the appliances 18 and 20 are positioned with the patient's upper and lower incisors vertically aligned. Scale 32 may be designed to measure relative movement of the appliances 18 and 20 with respect to each other in the A-P dimension on either side of the reference value. In one embodiment, a protrusive position of the mandible relative to zero corresponds to a positive number and a retrusive position of the mandible relative to zero corresponds to a negative number. The exact location of the reference value for a given patient may, in some embodiments, be experimentally determined, and may or not be indicated by the zero numeral on scale 32. However, in some embodiments, the zero numeral may be configured to indicate the vertical alignment of appliances 18 and 20 (that appliances 18 and 20 are aligned, as shown in FIG. 2). In other embodiments, scale 32 may vary. For example, the reference position may be indicated by the numeral 10, retrusive values may occupy or be indicated by numerical values in the range 0-10, and protrusive values occupy or be indicated by numerical range 10-20.

Figure 8:
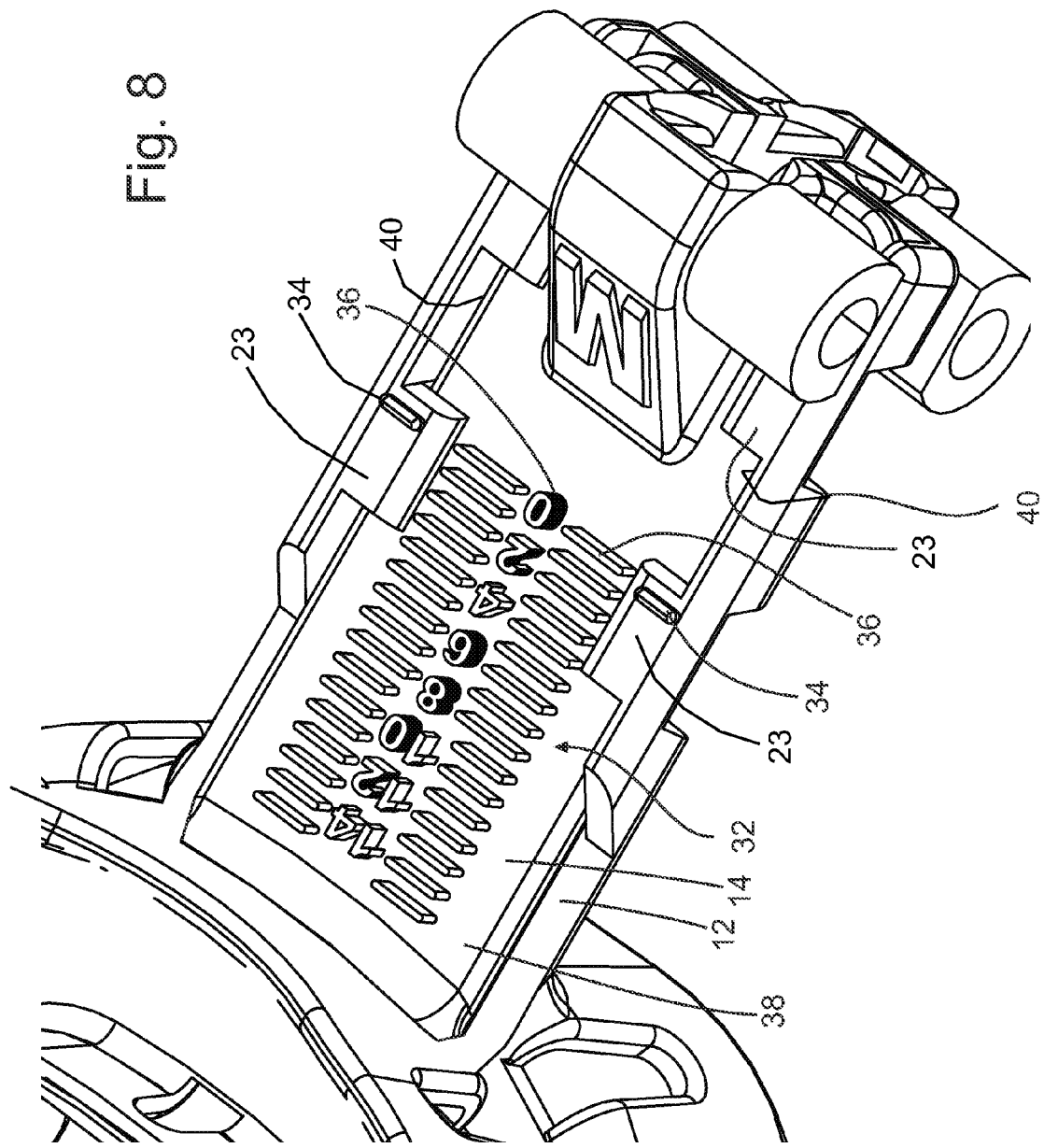
FIG. 8 is a perspective view of another embodiment of a relative position indicator that incorporates a ribbed displacement scale, and that is suitable for use in embodiments of the present mandibular protruders.

FIGS. 8 and 9 depict alternate embodiments of relative position indicators. In the embodiment of FIG. 8, lower bracket 14 comprises a scale 32 comprising ribbed elements 36, and upper mounting bracket 12 comprises a pointer 34 defined on a guide 23. Ribbed elements 36 may allow taking measurements to be more user-friendly, such as when reference pointer 34 is spaced vertically from a scale surface 38, as shown. For example, in the embodiment shown, ribbed elements 36 extend upward from scale surface 38 such that the tops of ribbed elements 36 are closer to pointers 34. In this embodiment, scale surface 38 is inserted in between wraparound edges 39 and 40 of lower mounting bracket 14 and/or between pointer(s) 34 of upper bracket 12. Scale surface 38 may be elongated and/or flattened to improve visibility.

In the embodiment of FIG. 9, the relative position indicator comprises: a scale 32 coupled to upper mounting bracket 12; and a window 41 extending through lower mounting bracket 14. More particularly, in this embodiment, upper mounting bracket 12 comprises a reference window 41 for viewing only a portion of a scale 32. In this embodiment, scale 32 is coupled to (e.g., integral with) an upper surface 42 of lower mounting bracket 14. In the embodiment shown, the relative position indicator is thus configured such that if upper mounting bracket 12 is coupled to lower mounting bracket 14 such that window 41 is within a range of scale 32 (such that a portion of scale 32 is viewable through window 41), scale 32 is viewable through window 41 to indicate a position of lower dental appliance 14 relative to upper dental appliance 12. In the embodiment shown, the relative position indicator further comprises a reference pointer 34 that is illustrated by markings 44 and/or includes slits 44 on one or both sides of window 41 such that if scale 32 is viewable through window 41, pointer 34 will indicate a position of lower dental appliance 18 relative to upper dental appliance 12. In other embodiments, pointer 34 may also or alternatively be digital, such as, for example a sensor and readout, a barcode reader-type electronic detection device. Other embodiments of reference pointer 34 may include a physical indicator that extends from rail (side 24 or edge surface 39) to rail (side 26 or edge surface 40) as a bar, or a pointer that comes up from the lower appliance 20 through a slot in the upper appliance 18.

Referring again to FIGS. 1-7, in the embodiment shown, protruder 10 comprises a drive motor 16 configured to effect or for effecting relative displacement of lower mounting bracket 14 and upper mounting bracket 12. More than one motor 16 may be used to effect such displacement. For example, in some embodiments (not shown), the present mandibular protruders can comprises a separate motor for each of brackets 12 and 14. In the embodiment shown, motor 16 comprises a linear actuator 17 configured to effect relative displacement of lower mounting bracket 14 and upper mounting bracket 12. In some embodiments, motor 16 is coupled more directly to one of upper mounting bracket 12 and lower mounting bracket 14 than to the other of upper mounting bracket 12 and lower mounting bracket 14. For example, in the embodiment shown, motor 16 is coupled more directly to upper mounting bracket 12 than the lower mounting bracket 14 (e.g., as a result of motor 16 being actuated, upper mounting bracket 12 and upper dental appliance 18 move relative to motor 16, while lower dental appliance 20 and lower mounting bracket 14 are not moved relative to motor 16). In other embodiments, motor 16 can be coupled more directly to lower mounting bracket 14.

In some embodiments motor 16 can be coupled to one of brackets 12 and 14 by a connector (or shaft or rod) 46, such as an actuator arm or rod of motor 16. The other of brackets 12 and 14 may be coupled or mounted directly or indirectly to motor 16 (e.g., to the body of motor 16 instead of linearly actuated connector 46), such that if the more-directly coupled bracket 12 or 14 is extended or retracted by motor 16, relative displacement is effected between appliances 18 and 20. For example, an indirect coupling may include coupling lower mounting bracket 14 to a housing of motor 16 instead of to connector 46). In the embodiment shown, connector 46 is coupled in contact with upper mounting bracket 12. In some embodiments, linear actuator 17 is configured to allow smooth and/or quiet movement bi-directionally in a single axis (horizontal in dimension or direction 27), which may be more comfortable to a patient than a stepping motor (e.g., may be less likely to wake a patient during use of protruder 10 in sleep titration study). However, in some embodiments, motor 16 may comprise a stepping motor or may be configured to be actuated or operated in a step-wise fashion. In some embodiments, linear actuator 17 may be limited to a maximum displacement, such as 20 mm, and/or may be configured to move in smooth minimum fine increments, such as, for example, 0.2 mm increments. Linear actuator 17 may comprise, for example, a Firgelli PQ12-63-6-P motor (available from Firgelli Technologies Inc., Vancouver, B.C., CANADA) that is lightweight and has an appropriate small footprint and box form factor for the protruder 10. Motor 16 may, for example, comprise a brushless and/or direct current (DC) motor. In other embodiments, motor 16 may comprise other suitable motors or actuators, such as, for example, a hydraulic piston.

In the embodiment shown, a mandibular positioning device 19 comprises and/or houses drive motor 16. Device 19 and brackets 12 and 14 are configured such that brackets 12 and 14 can be coupled to device 19, such as, for example, with or through connectors (or shafts or rods) 46 and 52, respectively. In the embodiment shown, upper mounting bracket 12 is configured to be coupled to connector 46 (e.g., drive-motor connector 46), and lower mounting bracket 14 is configured to be coupled to connector 52 (e.g., adjustment-mechanism connector 52, as discussed in more detail below). In the embodiment shown, connector 46 is configured to couple upper mounting bracket 12 (e.g., directly) to drive motor 16, and connector 52 is configured to couple lower mounting bracket 14 to device 19 such that if drive motor 16 extends and/or retracts bracket 12, bracket 14 remains stationary relative to device 19 and the housing of motor 16. In the embodiment shown, connector 52 is parallel to connector 46.

The one of the upper and lower mounting brackets 12, 14 that is coupled to be driven by motor 16 (in the embodiment shown, upper mounting bracket 12 and upper dental appliance 18), may be coupled to the motor 16 along the anterior-posterior axis 27 such that motor 16 can be actuated or activated to displace appliance 18 along the A-P direction 27. In this way, appliances 18 and 20 can be precisely and repeatably positioned relative to one another, and thus can precisely and repeatably protrude a patient's mandible relative to the patient's maxilla. During adjustment, drive motor 16 may effect relative displacement by extending or retracting connector 46 relative to device 19 such that device 19 is configured to push or pull a patient's mandible relative to the patient's maxilla. In the embodiment shown, extending connector 46 pushes the upper bracket 12 away from device 19 and causes drive motor 16 to move away from the patient. Due to a relatively static connection between drive motor 16 and lower mounting bracket 14 (e.g., via connector 52), lower mounting bracket 14 is simultaneously pulled, thereby pulling the patient's mandible (moving the patient's lower jaw with lower mounting bracket 14). The net effect is that a patient's lower jaw may be protruded forward (in an anterior direction) by exerting a backward force (in a posterior direction) on the upper jaw.

In the embodiment shown, mandibular positioning device 19 comprises a housing 48, such as a casing 48. Drive motor 16 and related components may be enclosed in casing 48, such as, for example, to protect drive motor 16 and patient from cross infection and bacteria. In some embodiments, casing 48 may be sealed and/or may be openable or removable (e.g., through an access door, such as shown on the back of housing 48, which may be attached and/or removable via screws, clips, tabs, or the like). For example, FIGS. 14C and 17C depict alternate embodiments of housings suitable for use with embodiments of the present devices 19. In some embodiments, casing 48 may be applied as a protective spray coating. In the embodiment shown (e.g., FIG. 2A), casing 48 houses or contains drive motor 16 and permits connectors 46 and 52 to extend out of casing 48. In the embodiment shown, connector 46 of motor 16 is configured to be coupled to a mounting bracket of a first dental appliance (e.g., upper mounting bracket 12 having upper dental appliance 18); and connector 52 is configured to be coupled to a mounting bracket of a second dental appliance (e.g., lower mounting bracket 14 having lower dental appliance 20).

In some embodiments, protruder 10 (e.g., device 19) comprises an initial position adjustment mechanism 50. In embodiments in which drive motor 16 is coupled more directly to one of brackets 12 and 14 (bracket 12 in the embodiment shown), the other of brackets 12 and 14 (bracket 14 in the embodiment shown) may be coupled to adjustment mechanism 50 (e.g., through connector 52). Initial position adjustment mechanism 50 is configured to be actuated to adjust the relative position of lower mounting bracket 14 and upper mounting bracket 12 (e.g., independently of drive motor 16). More particularly, in the embodiment shown, housing 48 is coupled to drive motor 16 and initial position adjustment mechanism 50; drive motor 16 is coupled between housing 48 and upper mounting bracket 12, and/or configured to adjust the relative position of lower mounting bracket 14 and upper mounting bracket 12 by adjusting the position of upper mounting bracket 12 relative to housing 48; and/or initial position adjustment mechanism 50 is coupled between housing 48 and lower mounting bracket 14, and/or configured to be actuated to adjust the relative position of lower mounting bracket 14 and upper mounting bracket 12 by adjusting the position of lower mounting bracket 14 relative to housing 48.

In this embodiments, protruder 10 is configured such that the position of upper dental appliance 18 with respect to (relative to) lower dental appliance 20 can be adjusted to a reference point (e.g., as a starting point from which a study of or for a patient can commence). This pre-adjustable reference point may be configured at a calibration time or step (e.g., before beginning a study), and/or then fixed in place before the study for the duration of the study. This reference point may be used to effectively zero or calibrate the device to a patient-specific reference retruded position. In some embodiments, the relative position indicator may be adjustable to point to zero on scale 32 when the protruder 10 is in the reference position. For example, in some embodiments, lower mounting bracket 14 can comprise an adjustable pointer 34 that can be adjusted or slid relative to lower mounting bracket 14 (e.g., relative to side 24 or 26) and/or upper mounting bracket 14 can comprise scale 32 that can be adjusted or slid relative to upper mounting bracket 12. Adjustable attachment of lower mounting bracket 14 to the housing of motor 16 can be accomplished by a variety of methods and/or with a variety of structures or configurations.

Figure 1B:
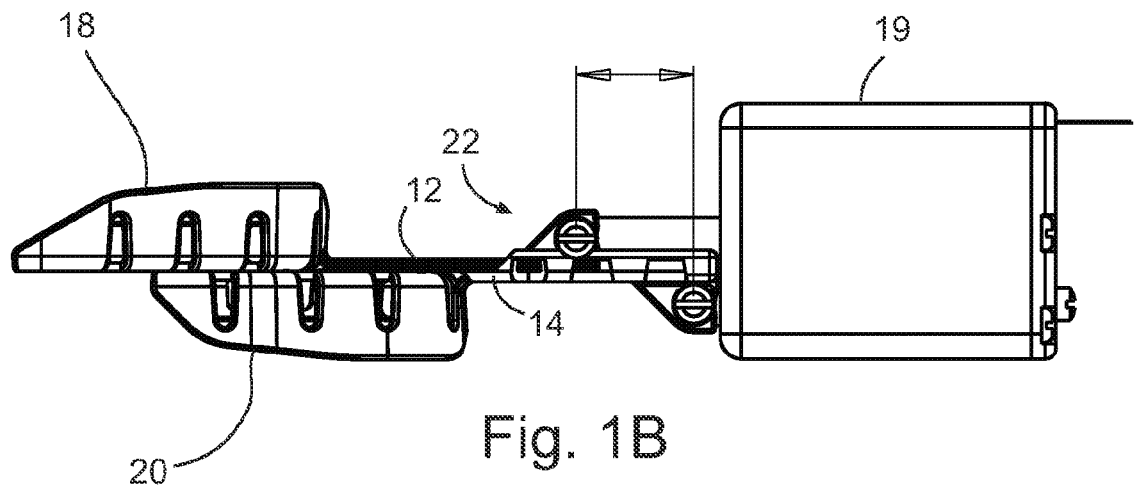
Figure 1C:
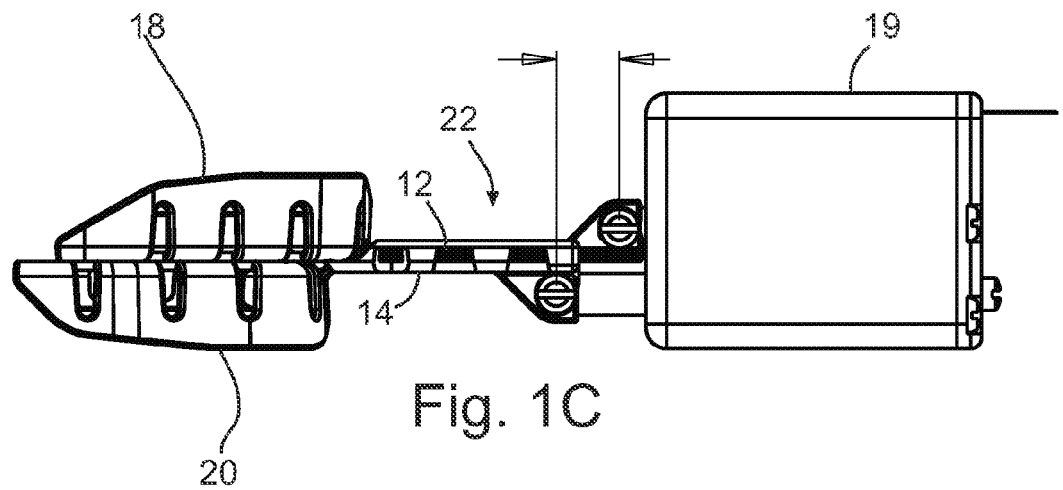

For example, in the embodiment shown (e.g., FIGS. 6A and 6B), initial position adjustment mechanism 50 comprises a manually operable element, such as, for example, a screw 54 and/or a knob 56 coupled to screw 54 such that knob 56 can be rotated outside housing or casing 48 to rotate screw 54 inside housing 48. In this way, adjustment mechanism 50 is configured such that turning a rotational external fixture, such as knob 56, rotates screw 54 to mechanically adjust the position of connector 54 (and thereby lower dental appliance 20) along the anterior-posterior axis 27 (FIG. 1A). This allows the start or initial relative position of the appliances 18, 20 to be accurately and reproducibly achieved before initiating a study of a patient. Screw 54 (and thereby knob 56) can be coupled to an end 53 of connector 54. For example, end 53 of connector can be provided with female or internal threads corresponding to male or external threads of screw 54, and screw 54 can be rotatably coupled to housing 48 such that screw 54 is linearly fixed relative to housing 48, such that rotation of screw 54 will translate into linear displacement of connector 52. As shown in FIGS. 1A and 1B, the depicted initial position adjustment mechanism 50 is configured to allow positioning of lower appliance 20 to a retruded position in which upper appliance 18 is retracted relative to housing 48 (e.g., in which lower mounting bracket 14 is as close to housing 48 as permitted). As shown in FIG. 1C, when upper appliance 18 fully retracted and lower appliance 20 fully is extended, the full stroke of the drive motor 16 (FIG. 6A) is available for protruding a patient's mandible from the fully retruded position. FIG. 1A shows both of appliances 18 and 20 fully retracted, while FIG. 1B shows the protruder 10 in a maximally protruded position or configuration in which appliance 18 is fully extended and appliance 20 is fully retracted relative to device 19 (housing 48).

In some embodiments, connector 52 and/or housing 48 are configured to resist rotation of connector 52 relative to housing 48. For example, in the embodiment shown, connector 52 comprises longitudinal protrusions 55 that are aligned with the longitudinal axis of connector 52, and housing or casing 48 comprises grooves 57 configured to receive protrusions 55 such that connector 52 can move linearly relative to housing 48 but is constrained to linear motion (e.g., such that protrusions 55 and grooves 57 cooperate to prevent connector 52 from rotating relative to housing 48). In other embodiments, other initial position adjustment mechanisms may be used, such as, for example, motorized mechanisms. In the embodiment shown, adjustment mechanism 50 further comprises a locking nut 67 configured to prevent screw 54 from moving in the A-P direction relative to housing 48. For example, in some embodiments, the threads of nut 67 are provided or coated with an adhesive or the like such that screw 54 can be threaded into nut 67 to assemble adjustment mechanism 50 and/or device 19, but then becomes fixed relative to nut 67 to maintain the linear position of screw 54 relative to housing 48 while still permitting rotation of screw 54 relative to housing 48.

Additionally, in the embodiment shown, housing 48 has a sidewall with at least a first opening (corresponding to connector 46) and a second opening (corresponding to connector 52). In this embodiment, housing 48 is coupled to drive motor 16 and adjustment mechanism 50 such that housing 48 encloses at least a portion of each of drive motor 16 and adjustment mechanism 50, and such that drive-motor connector 46 extends out of housing 48 through the first opening, and adjustment-mechanism connector 52 extends out of housing 48 through the second opening. In the embodiment shown, adjustment mechanism 50 is configured to linearly adjust the position of adjustment-mechanism connector 52; and drive motor 16 is configured to linearly move drive-motor connector 46 in a direction substantially parallel to the direction in which adjustment mechanism 50 can adjust adjustment-mechanism connector 52.

As shown FIG. 3A, and as noted above, upper dental appliance 18 may comprise an upper dental tray 58, and lower dental appliance 20 may comprise a lower dental tray 60. Appliances 18 and 20 may include upper and lower arches, respectively, that fit into a patient's mouth and/or receive a patient's teeth (e.g., a portion of a patient's teeth) to hold or couple to the patient's jaws. Mounting brackets 12 and 14 extend out from with appliances 18 and 20, respectively. In some embodiments of the present mandibular protruders, upper dental appliance 18 is integral with, for example molded as a part of, upper mounting bracket 12. Similarly, in some embodiments, lower dental appliance 20 is integral with, for example molded as a part of, lower mounting bracket 14. In other embodiments, appliances 18 and 20, and their respective mounting brackets 12 and 14 may be coupled together as separate parts. Appliances 18 and 20 may be U-shaped disposable or non disposable appliances for a patient's upper and lower jaws, respectively. In some embodiments (e.g., FIG. 10), appliances 18 and 20 may comprise at least a partial mould of a patient's teeth. For example, appliances 18 and 20 may be filled with a quick-set material, such as boil-and-bite insert 62, which may be used to take fast custom impressions. For example, materials such as a silastic impression material (e.g., PolyFil™ TransBite available from SciCan™ Medtech AG, Cham, Switzerland) and/or a thermoplastic impression material may be used. In some embodiments (e.g., embodiments in which appliances 18 and/or 20 (e.g., trays 58 and/or 60) are intended to be disposable, the present kits can comprise a positioning device 19 and a plurality of appliances 18 and/or 20 (e.g., trays 58 and/or 60).

As discussed below, some embodiments comprise: dental impression material configured to be coupled to at least one of the upper dental appliance and the lower dental appliance, the dental impression material configured to be imprinted with and maintain an impression of a patient's teeth. A patient may be fitted with appliances 18 and 20 in his or her natural resting or normal bite position, in order to establish the reference position in some cases. The position of appliances 18 and 20 may be secured together, such as by clipping together, to preserve this relative position of upper and lower appliances 18 and 20. In the embodiment shown, tray walls 63 and 65 of appliances 18 and 20, respectively, include slits 64 throughout to import greater flexibility and/or to permit dental impression material to extrude or extend through slits 64 to improve stability of the dental impression material (e.g., insert 62) relative to appliances 18 and 20. Walls 63 and 65 may also provide improved retention of insert 62. Appliances 18 and 20 may also be configured to maximize fit and comfort, and minimize encroachment on lingual space. Front portions 66 and 68 of appliances 18, 20 may be narrower than respective back or lateral portions 70 and 72 (e.g., to fit the natural size of the teeth). In the embodiment shown, appliances 18 and 20 are each configured to permit lateral portions (e.g., 70, 72) to flex relative to the front portions 66 and 68 (e.g., via slits between the front portions and the lateral portions. Inner tray walls 63A and 65A may be half the height of outer tray walls 63B and 65B of appliances 18 and 20, respectively, (e.g., to provide a better fit and comfort and/or provide greater stability for upper appliance 18 during movement (e.g., upon activation of motor 16). In some embodiments, appliances 18 and 20 may be designed and/or configured to such that the molar arms (lateral portions) of the trays spring laterally (are biased in a lateral, outward direction) so the inner wall of the trays are applied firmly (tend to press against) to the lingual surface of the molars and thereby minimize encroachment into the lingual space. In some embodiments, appliances 18 and 20 are flexible and/or smaller in size than existing dental trays (e.g., to improve comfort or fit for a patient). As illustrated (e.g., in FIGS. 1A-1C and 6A-6B), upper mounting bracket 12 may include a planar portion extending anteriorly along a plane defined by inferior (lower) surface or aspect 70 of upper dental appliance 18 and/or lower mounting bracket 14 may include a planar portion extending anteriorly along a plane defined by superior (upper) aspect or surface 72 of lower dental appliance 20, as shown.

In the embodiment shown, and as noted above, appliances 18 and 20 are coupled to mandibular positioning device 19 through brackets 12 and 14, respectively. In the embodiment shown, upper mounting bracket 12, lower mounting bracket 14, and rail system 22 are configured to be removably coupled to drive motor 16 (and/or positioning device 19). More particularly, in the embodiment shown, drive-motor connector 46 has a longitudinal axis that is substantially parallel to the direction of actuation (e.g., A-P direction 27) of drive motor 16, and one of upper mounting bracket 12 and lower mounting bracket 14 (as shown, upper mounting bracket 12) is configured to be coupled to drive-motor connector 46 such that the longitudinal axis of the one of upper mounting bracket 12 and lower mounting bracket 14 (as shown, upper mounting bracket 12) is substantially parallel to (and, in some embodiments, co-linear with) the longitudinal axis of drive-motor connector 46. As shown in FIGS. 3A and 3B, in some embodiments, such as the embodiment shown, mandibular protruder 10 may include an upper release mechanism (e.g., a nut 74 and bolt 76 arrangement for passing through bracket 12 and connector 46), for release of upper dental appliance 18 from device 19 (shown in FIG. 4). Similarly, mandibular protruder 10 may incorporate a lower release mechanism (e.g., a nut 78 and bolt 80 arrangement for passing through bracket 14 and connector 52), for release of lower dental appliance 20 from mandibular positioning device 19. In other embodiments, nuts 74 and/or 78, and/or bolts 76 and/or 80, may include and/or may instead comprise any suitable fastener, such as, for example, a wing-nut or wing-bolt that can be tightened or loosened by hand (without additional tools), a pin and/or a cotter pin, and/or the like. In some embodiments, upper mounting bracket 12 and/or lower mounting bracket 14 may be threaded on at least one side of connector 46 or 52, such that no nuts are needed to tighten or hold bolts 76. In some embodiments, bolts 76 and/or 80 comprise screws (not shown) such that the nuts are omitted.

In some embodiments, upper mounting bracket 12 is configured to be coupled to a connector (e.g., 46 or 52) of an initial adjustment mechanism 50 or a drive motor 16, and lower mounting bracket 14 is configured to be coupled to a connector (e.g., 46 or 52) of an initial adjustment mechanism 50 or a drive motor 16. For example, in the embodiment shown, upper mounting bracket is configured to be coupled to connector 46, and lower mounting bracket 14 is configured to be coupled to connector 52. More particularly, in the embodiment shown, adjustment-mechanism connector 46 includes a longitudinal axis, a proximal portion 82A having a first cross-section, and a distal portion 82B having a second cross-section that is different than the first cross-section; and drive-motor connector 52 includes a longitudinal axis, a proximal portion 84A having a first cross-section, and a distal portion 84B having a second cross-section that is different than the first cross-section. More particularly, in the embodiment shown, first cross-sections of proximal portions 82A and 84A are circular, and second cross-sections of distal portions 84A and 84B have parallel sides (e.g., are similar to rectangles with curved upper and lower perimeters). In some embodiments, connectors 46 and 52 are configured with different sizes and/or cross-sectional shapes so that at least one of connectors 46 and 52 will only couple to one of upper mounting bracket 12 and lower mounting bracket 14. For example, in some embodiments, distal portion 82B of connector 46 is wider than distal portion 84B of connector 52. In the embodiment shown, adjustment-mechanism connector 52 includes a hole 81 extending through distal portion 84B transverse to the longitudinal axis of adjustment-mechanism connector 52; and drive-motor connector 46 includes a hole 77 extending through distal portion 82B transverse to the longitudinal axis of drive-motor connector 46. In this embodiment, connectors 46 and 52 are configured to be coupled to brackets 12 and 14 having respective recesses that correspond to the shape of connectors 46 and 52 (e.g., to improve the strength of connection to between brackets 12 and 14, and connectors 46 and 52, respectively.

Similarly, as illustrated, for example, in FIGS. 3A and 3B, upper mounting bracket 12 has a longitudinal axis and a recess 73 configured to receive a portion of connector 46. Recess 73 has an outer portion with a first cross-section (corresponding to first cross-section of proximal portion 82A), an inner portion having a second cross-section (corresponding to second cross-section of distal portion 82B) that is different than the first cross-section, and a hole 75 extending transverse to the longitudinal axis of upper mounting bracket 12, and through upper mounting bracket 12 across the inner portion of recess 73. Similarly, lower mounting bracket 14 has a longitudinal axis and a recess 83 configured to receive a portion of connector 52. Recess 75 has an outer portion with a first cross-section (corresponding to first cross-section of proximal portion 84A), an inner portion having a second cross-section (corresponding to second cross-section of distal portion 84B) that is different than the first cross-section, and a hole 79 extending transverse to the longitudinal axis of lower mounting bracket 14, and through lower mounting bracket 14 across the inner portion of recess 75.

To couple dental appliance 18 to connector 46, connector 46 may be slid into recess 73, which may be molded as part of bracket 12. Bolt 76 may then be passed through hole 75 of bracket 12, and hole 77 of connector 46. Nut 74 may then be used to secure bolt 76 in place. Similarly, to couple appliance 20 to connector 52, connector 52 may first be slid into recess 83, which may be molded as part of bracket 14. Bolt 80 may then be passed through hole 79 of bracket 14, and hole 81 of connector 52. Nut 78 is then used to secure bolt 80 in place. In the embodiment shown, holes 77 and 81 pass through the width of connectors 46 and 52, respectively, and align with holes 75 and 79 in recesses 73 and 83, respectively. Nut 74 can be tightened sufficiently to prevent vertical tilting of upper tray 18, or can be tightened to a degree that permits some vertical tilting of tray 18 (e.g., within the tolerances of rail system 22). Bolt 76 and 80 sizing may be chosen to ensure a tight fit with respective holes 75 and 79 to ensure that little or no movement is possible between device 19 and appliances 18 and 20 (e.g., to rigidly fixed the components of protruder 10 together). Tilting may also be restricted by rail system 22 (e.g., portions of mounting brackets 12 and 14, and/or appliances 18 and 20, may be flush and planar to each other). The encapsulation of connectors 46 and 52, by recesses 73, 83, respectively, provide structures that are configured to prevent rotation about coronal axis 28. In these and other embodiments, appliances 18 and 20 and brackets 12 and 14 are disposable. Other releasable connection points may be used, such that at least appliances 18 and 20 may be disposable. In some embodiments, protruder 10 itself is fully or partially disposable. Various components of protruder 10 (e.g., brackets 12 and 14, connectors 46 and 52, and/or housing 48) can comprise acetal-based plastics, such as, for example, Polyoxymethylene (POM).

The general operation of the mandibular protruder 10 may be illustrated with reference to FIGS. 1A-C. Beginning at the retruded position shown in FIG. 1A, a protrusion of the mandible is achieved by extending connector 46, thereby exerting an inward force on upper dental appliance 18. A comparable and opposite protruding force is thus exerted on lower dental appliance 20. As shown in FIG. 1B, these forces cause protrusion of the mandible with respect to the maxilla and the rest of the skull (e.g., through protrusion of lower dental appliance 20 relative to upper dental appliance 18). As shown in FIG. 1C, for retrusion of the mandible, the reverse occurs: connector 46 retracts, and thereby exerts an outward or pulling force on upper appliance 18 and an opposite pushing or retruding force on lower appliance 20. As described above, this will, for most patient's, cause a retrusion of the mandible.

Referring to FIGS. 11 and 12, FIG. 11 depicts a schematic of one embodiment of the present systems for carrying out a sleep titration on a patient with a mandibular protruder 10, and FIG. 12 depicts a flowchart of one method of displacing a patient's mandible 88 relative to the patient's maxilla 90. In a stage or step 100, the position of one of brackets 12 and 14, in this case lower bracket 14, is relatively adjusted to an initial position. This may be done with the initial position adjustment mechanism 50, as discussed above. Stage or step 100 may be performed or carried out before or after protruder 10 is in place in the patient's mouth. As discussed, the initial position may comprise a rest position where the mandible is protruded somewhat relative to a fully retruded position. In some embodiments, the initial position may be a comfortable neutral position for the patient. For example, in some embodiments, step 100 can comprise adjusting the relative position of one of an upper mounting bracket 12 having an upper dental appliance 18, and a lower mounting bracket 14 having a lower dental appliance 20. For example, in the embodiment shown above, the relative position of lower mounting bracket 14 can be adjusted (independently of motor 16) by rotating screw 54 (e.g., via knob 56).

In a stage or step 102 (shown in FIG. 12), the other of brackets 12 and 14, in this case bracket 12, is relatively displaced with drive motor 16 (e.g., as in FIG. 6A) to cause relative displacement between appliances 18 and 20, and to displace (e.g., protrude or retrude), the patient's mandible 88. Step 102 may be accomplished as part of a sleep titration carried out to determine a mandibular protrusion effective in treating obstructive sleep apnea. The effective mandibular protrusion may be determined from a relative position indicator of appliances 18, 20, as discussed above. In a further stage or step, a mandibular protrusion oral appliance, such as a retainer (not shown), may be constructed, adjusted, and/or calibrated for the patient based on the results of the sleep titration. For example, in some embodiments, step 102 can comprise relatively displacing with a drive motor 16 the other of upper mounting bracket 12 and lower mounting bracket 12 when a patient's upper teeth are disposed in (or otherwise coupled to) upper dental appliance 18 and patient's lower teeth are disposed in (or otherwise coupled to) lower dental appliance 20 to cause relative displacement of upper dental appliance 12 and lower dental appliance 14 and displace the patient's mandible relative to the patient's maxilla. For example, in the embodiment shown, motor 16 can be activated to displace upper mounting bracket 12 relative to housing 48 such that lower mounting bracket 14 and lower dental appliance 20, and a patient's mandible, are displaced relative to the patient's maxilla. For example, relatively displacing the other of upper mounting bracket 12 and lower mounting bracket 14 can protrude the patient's mandible relative to the patient's maxilla.

In some embodiments, relatively displacing is repeated while the patient's breathing is monitored and/or may be performed responsive to detection of an interruption in the patient's breathing. As also described in more detail below, some embodiments of the present methods further comprise: determining an optimal mandibular displacement for the patient at which the patient experiences less than a predetermined maximum number of respiratory disturbances in a period of time. For example, in some embodiments, the maximum number of respiratory disturbances corresponds to a respiratory disturbance index (RDI) (e.g., the predetermined maximum number of respiratory disturbances can correspond to an RDI of 10 per hour and/or an RDI that is less than a baseline RDI for the patient). In some embodiments, the period of time is 10 minutes. In some embodiments, the predetermined number of respiratory disturbances corresponds to no snoring and/or no inspiratory flow limitation (e.g., during rapid eye movement (REM) sleep) and/or is measured when the patient is supine). In some embodiments, the optimal mandibular protrusion is determined from a relative position indicator that indicates relative position of lower dental appliance 14 and upper dental appliance 12. The protruder 10 may be used by a physician or other user to determine an optimal mandibular displacement (e.g., from the patient's natural or resting mandibular position), such that some embodiments of the present methods comprise: communicating the optimal mandibular displacement for the patient to an entity (e.g., a dentist) for construction of a mandibular protrusion oral appliance for the patient.

Some embodiments of the present methods comprise: providing a mandibular protruder 10 (e.g., any of the present embodiments of protruder 10, such as one comprising: an upper mounting bracket 12 having an upper dental appliance 18; a lower mounting bracket 14 having a lower dental appliance 20; a rail system 22 coupling upper mounting bracket 12 to lower mounting bracket 14 such that relative displacement of lower mounting bracket 14 and upper mounting bracket 12 is constrained to linear motion in an anterior-posterior direction; a drive motor 16 configured to effect relative displacement of lower mounting bracket 12 and upper mounting bracket 14; and an initial position adjustment mechanism 50 configured to be actuated to adjust the relative position of lower mounting bracket 14 and upper mounting bracket 12 independently of drive motor 16); actuating initial position adjustment mechanism 50 to adjust the relative position of upper mounting bracket 12 and lower mounting bracket 14; and relatively displacing with drive motor 16 upper mounting bracket 12 and lower mounting bracket 14 when a patient's upper teeth are coupled to (e.g., disposed in) upper dental appliance 18 and patient's lower teeth are coupled to (e.g., disposed in) lower dental appliance 20 to cause relative displacement between upper dental appliance 12 and lower dental appliance 20 and displace the patient's mandible relative to the patient's maxilla.

For example, an overview of an exemplary use of the present protruders (e.g., 10) and/or systems (e.g., as shown in FIG. 11) may go as follows. A dentist or physician may register numerical values, for example on scale 32, corresponding to the fully retruded and fully protruded position of the mandible of a patient. The most convenient zero value of the scale may occur when the upper and lower incisors are positioned opposite each other, i.e. "end-to-end" position of the mandible 88 relative to the maxilla 90. With appliances 18 and 20 positioned on the teeth and secured by for example impression material, the dentist may record the reading on scale 32 at the fully retruded position and fully protruded position. These values and appliances 18 20 may be given to a technologist who then enters the values into a controlling computer (workstation 92). Workstation 92 has a software component that allows for the technician to regulate the device. The software in the computer is configured to accept the fully retruded, fully protruded, and "rest" scale readings, and to calculate the position of mandible 88 with these values. Appliances 18 and 20 are then attached to device 19, and adjustment mechanism 52 of device 19 can be adjusted to the determined rest position or a nominal rest position for comfort (for example fully retruded plus a fixed number of millimeters, e.g., 1, 2, 3, 4, etc. mm). A study (e.g., sleep titration) can be performed (e.g., by a technician) to determine an optimal mandibular displacement for the patient (e.g., a mandibular displacement in which the patient experiences the fewest number of respiratory disturbances) by inputting a command at workstation 92 each time the technician decides or desires to relatively displace (e.g., by an incremental displacement) the patient's mandible relative to the patient's maxilla with drive motor 16 (e.g., while the patient is monitored via PSG device 96). The optimal mandibular displacement (e.g., the target therapeutic distance) such as, for example, relative to zero, can be noted by the technologist at the end of the study and transmitted with appliances 18 and 20 back to the dentist.

In a further example, the patient first visits the dentist to obtain disposable trays 58 and 60. Some embodiments of the present methods comprise fitting the patient with small, medium, or large trays. Some embodiments comprise filling trays 58 and 60 with Blue-Mousse (Parkell Dental, U.S.A.), boil-and-bite inserts 62, hardening agent, thermoplastic impression material, and/or the like; inserting top tray 58 into the patient's mouth, and/or inserting bottom tray 60 into the patient's mouth (e.g., while rail system 22 is engaged or coupled upper mounting bracket 12 to lower mounting bracket 14). The patient can be asked to bite down, such as to imprint the material and/or permit the material to harden or quick set. The patient can be asked to move the jaw to a fully retruded position of the patient's mandible. Some embodiments comprise reading scale 32 (shown in FIG. 7) on top of upper bracket 12 to determine and/or registering (e.g., recording) a relative position value corresponding to the fully retruded position. The patient can be asked to move the jaw to a fully protruded position. Some embodiments comprise reading scale 32 to determine and/or registering a relative position value corresponding to the fully protruded position of the patient mandible. The patient can be asked to move the jaw to a rest position. Some embodiments comprise reading scale 32 to determine and/or registering a relative position value corresponding to the rest position of the patient's mandible. Some embodiments comprise removing tray 58 and/or 60. For example, if trays 58 and 60 are individually removed, bottom tray 60 may be removed first. Some embodiments comprise communicating or transferring the scale readings (e.g., retruded, protruded, rest) and/or trays 58 and 60 to another entity (e.g., sleep technician). In some embodiments (e.g., embodiments for prolonged therapeutic use), the dental impression material is configured to be durable such that the dental impression material will substantially hold its shape for use up to 1, 2, 3, 6, and/or 12 months. In such embodiments, the dental impression material may be molded to a user's teeth, removed from the patient, and cured or otherwise hardened (e.g., with heat, ultraviolet light, etc.)

Some embodiments of the present methods comprise receiving (e.g., from a dentist) trays 58 and 60 for a patient. Some embodiments comprise coupling (e.g., via rail system 22) upper tray 58 and lower tray 60; coupling upper tray 58 to device 19 (e.g., to motor 16) via connector 46 (e.g., in a fully retracted position flush to housing 48 of device 19); and/or coupling lower tray 60 to device 19 (e.g., to adjustment mechanism 50) via connector 52. Some embodiments comprise adjusting connector 52 (e.g., via adjustment mechanism 50) to ensure that pointer 34 reads at the reference position of scale 32. In some embodiments, the reference position is the fully retruded position. In other embodiments, the reference position is fully retruded plus a fixed and repeatable nominal amount, such as, for example, equal to, less than, or between, any of: 1, 2, 3, 4, or 5 mm. The additional adjustment may be chosen to provide patient comfort as the patient may not be comfortable in the fully retruded position. Some embodiments comprise storing the retruded, protruded, and rest scale readings for the patient in the computer workstation 92 (e.g. in a storage device of workstation 92).

Some embodiments comprise inserting trays 58 and 60 into the patient's mouth (e.g., together). Some embodiments comprise performing a sleep titration test on the patient. In the embodiment shown, controller 94 may be controlled by workstation 92 to provide control of protruder 10 (e.g., to control relative position of upper mounting bracket 12 and lower mounting bracket 14). For example, in some embodiments, controller 94 is configured to transmit signals to the drive motor to cause the drive motor to effect relative displacement of the lower mounting bracket and the upper mounting bracket (e.g., to activate the drive motor to displace the upper bracket relative to the housing such that the lower mounting bracket and the patient's mandible are displaced relative to the patient's maxilla). In some embodiments controller 94 is also configured to sense the relative position of the lower mounting bracket and the upper mounting bracket, and to transmit (e.g., to workstation) and/or record one or more signals indicative of the position of the lower mounting bracket relative to the upper mounting bracket. In other embodiments, controller 94 comprises a user-input device to permit a user to adjust the relative displacement of upper dental appliance 18 and lower dental appliance 20 by inputting a command directly to controller 92.

In some embodiments, controller 94 is integral with workstation 92, and/or workstation 92 is configured to control protruder 10 directly. In some embodiments, controller 94 is configured to power protruder 10 (e.g., controller 94 can include a power source such as one or more batteries and/or a medical-grade alternating current (AC) power source). Additionally, controller 94 and/or workstation 92 may be coupled to a polysomnogram 96 (PSG), and/or may be configured to provide or send input signals to track protruder 10 status (e.g., relative position of upper and lower mounting brackets 12 and 14 or dental appliances 18 and 20).

In the present embodiments, protruder 10 may be referred to as a remote-control mandibular protruder (RCMP) in which the relative displacement during use (e.g., displacement that is effected by the drive motor, as opposed initial adjustments effected by the initial position adjustment mechanism) is actuated or controlled by a motor or other actuator instead of by physical actuation of the dental appliances or mounting brackets by a user. For example, in the embodiments shown, the motor is activated or controlled by a control signal or by application of a voltage to the motor. In some embodiments, the RCMP (protruder 10) may allow for a level 1 sleep titration with an oral appliance where the patient will not be disturbed or awakened. Some embodiments comprise: remotely adjusting protruder 10 while monitoring and/or responsive to the PSG, such as, for example, to determine optimal settings for the protruder (e.g., similar in some respects to a level 1 CPAP). This may therefore allow a sleep physician to diagnose and/or recommend oral appliances, such as, for example, for patients who do not respond to or do not use a CPAP (e.g., upon CPAP non-compliance).

Some embodiments of the present methods comprises communicating or transmitting the results of the sleep titration to an entity (e.g., a dentist), such as, for example, in the form of either a scale reading or protrusion amount (e.g., an optimal mandibular displacement), such as, for example, from either max retrusion or distance from when the teeth are end to end. Some embodiments of the present methods comprises receiving and/or accessing the results of the sleep titration (e.g., performed using one or more of the present protruders, positioning devices, and/or apparatuses) from, for example, an entity (e.g., a dentist or physician). Some embodiments comprise producing, prescribing, and/or ordering an oral appliance based on the results (e.g., an oral appliance for the patient with the optimal mandibular displacement). Some embodiments comprise adjusting and/or calibrating an oral appliance (e.g., a commercially-available oral appliance, such as, for example, a MAS appliance available from SomnoMed, Canada, U.S.A., Australia) to have a mandibular displacement corresponding to an optimal mandibular displacement. In some embodiments, trays 58 and 60 may be used in and/or may be used to make or produce the oral appliance. For example, upper and lower trays 58 and 60 can be coupled with a screw, clamp, adhesive, or the like to statically fit together at a specified displacement (e.g., optimal mandibular displacement). After the patient has been given the produced oral appliance, such as a mandibular protrusion retainer, check-ups may be carried out as desired to ensure useful functioning. Some embodiments of the present oral appliances comprise an oral appliance that has been adjusted to cause an optimal mandibular displacement when worn by a patient, the optimal mandibular displacement for the patient having been determined by a sleep titration performed with an embodiment of the present protruders, devices, and/or systems.

In some embodiments, controller 94 may include and/or house batteries sufficient to motorize the protruder 10, and electronics sufficient to control or send control signals to protruder 10 and/or transmit data (e.g., to workstation 92 or PSG device 96). Controller 94 may be coupled to (e.g., in electronic communication with) protruder 10 via a cable and may be expected to reside under a pillow or on a night stand during the patient study. Protruder 10 may have a wired or wireless bidirectional connection to a control module (e.g., workstation 92 or other control module) that allows a technician to alter the displacement amounts and regulate device status from another room. Protruder 10 may also have a unidirectional connection to a PSG 96 to permit logging of activity over time and generation of a single inclusive report or data stream (e.g., to workstation 92), which may include a single or multiple output jack, such as, for example, similar to output jacks on CPAP machines, which will interface with PSG devices 96 to provide data output.

Workstation 92 may include the software component with which a technician interfaces to control and receive status information on protruder 10. Workstation 92 and/or appropriate software may be configured to communicate with controller 94 either wired or wirelessly to provide or enable bi-directional status and control data. The software may be configured to display status information like force and position, as well as control movement or position of protruder 10 to retract or extend lower appliance 20 and the patient's mandible relative to upper appliance 18 and the patient's maxilla. The software component may comprise an application configured to separately or solely control protruder 10 (as opposed to jointly controlling protruder 10 and PSG device 96), and may, for example: include the capability to increase or decrease relative displacement of lower appliance 20 relative to upper appliance 18; set the increments at which to move linear actuator 17 of motor 16; and/or reset protruder 10

(e.g., lower appliance 20) to the rest position. The software may also be configured to include safety features and restrictions on protruder 10, such as, for example, to prevent extending or retracting the jaw beyond pre-set limits and/or to prevent protruder 10 from exerting a force on mandible in excess of a predetermined maximum (e.g., a force equivalent to 2 kilograms).

Coupling components may be achieved through additional unmentioned parts, structures, or configurations that permit the components to be coupled in the manner described. Two components that are coupled may include the two components being integral with one another, if such a configuration would permit the two components to interrelate in the manner claimed. When a first component has or includes a second component, it can include embodiments in which the first and second components are connected together or through other parts. Also, it should be understood that various portions or components of embodiments disclosed herein may be used in other embodiments disclosed herein. For example, the present disclosure includes embodiments of mandibular protruders, mandibular positioning devices that may be suitable for use in embodiments of the present mandibular protruders, and apparatuses that may be suitable for use with embodiments of the present mandibular positioning devices and/or in embodiments of the present mandibular protruders.

In one example, the present disclosure includes various embodiments of a mandibular protruder (e.g., 10) comprising: an upper mounting bracket 12 having an upper dental appliance 18; a lower mounting bracket 14 having a lower dental appliance 18, the lower mounting bracket configured to be coupled to the upper mounting bracket such that relative motion of the lower mounting bracket and the upper mounting bracket is constrained to linear motion in an anterior-posterior direction; a mandibular positioning device 19 configured to be coupled to upper mounting bracket 12 and lower mounting bracket 14, the mandibular positioning device having a drive motor 16 configured to adjust the relative position of lower mounting bracket 14 and upper mounting bracket 12 if the mandibular positioning device is coupled to upper mounting bracket 12 and lower mounting bracket 14; an upper release mechanism configured to release upper dental appliance 18 from mandibular positioning device 19 if mandibular positioning device 19 is coupled to upper mounting bracket 12; and a lower release mechanism configured to release lower dental appliance 20 from mandibular positioning device 19 if mandibular positioning device 19 is coupled to lower mounting bracket 14.

In another example, the present disclosure includes various embodiments of a mandibular protruder (e.g., 10) comprising: an upper mounting bracket 12 having an upper dental appliance 18; a lower mounting bracket 14 having a lower dental appliance 20, the lower mounting bracket configured to be coupled to the upper mounting bracket such that the lower mounting bracket can move linearly relative to the upper mounting bracket; a drive motor 16 coupled to one of upper mounting bracket 12 and lower mounting bracket 14, the drive motor configured to effect relative displacement of lower mounting bracket and the upper mounting bracket; and an initial position adjustment mechanism 50 configured to adjust an initial position of the other of the upper mounting bracket and the lower mounting bracket.

In another example, the present disclosure includes various embodiments of a mandibular positioning device (e.g., 19) comprising: a drive motor 16 having a connector 46 configured to be coupled to a mounting bracket (e.g., 12 or 14) of a first dental appliance (e.g., 18 or 20); an adjustment mechanism 50 having a connector 52 configured to be coupled to a mounting bracket (e.g., 12 or 14) of a second dental appliance (e.g., 18 or 20); and a housing 48 having a sidewall with at least a first opening and a second opening, the housing coupled to drive motor 16 and the adjustment mechanism 50 such that the housing encloses at least a portion of each of the drive motor and the adjustment mechanism, the drive-motor connector extends out of the housing through the first opening, and the adjustment-mechanism connector extends out of the housing through the second opening. In some embodiments, adjustment mechanism 50 is configured to linearly adjust the position of the adjustment-mechanism connector. In some embodiments, drive motor 16 is configured to linearly move the drive-motor connector in a direction substantially parallel to the direction in which the adjustment mechanism can adjust the adjustment-mechanism connector.

In another example, the present disclosure includes various embodiments of an apparatus for use with a mandibular positioning device (e.g., 19), the apparatus comprising: an upper mounting bracket 12 having an upper dental appliance 14; a lower mounting bracket 14 having a lower dental appliance 20, the lower mounting bracket configured to be coupled to the upper mounting bracket such that relative linear motion of the lower mounting bracket and the upper mounting bracket is permitted; and a relative position indicator for indicating relative position of the lower dental appliance and the upper dental appliance; where the apparatus is configured such that the lower mounting bracket can be coupled to the upper mounting bracket and such that the upper mounting bracket and the lower mounting bracket can be independently coupled to a first connector (e.g., 46) and a second connector (e.g., 52) respectively of a mandibular positioning device.

Figure 13:
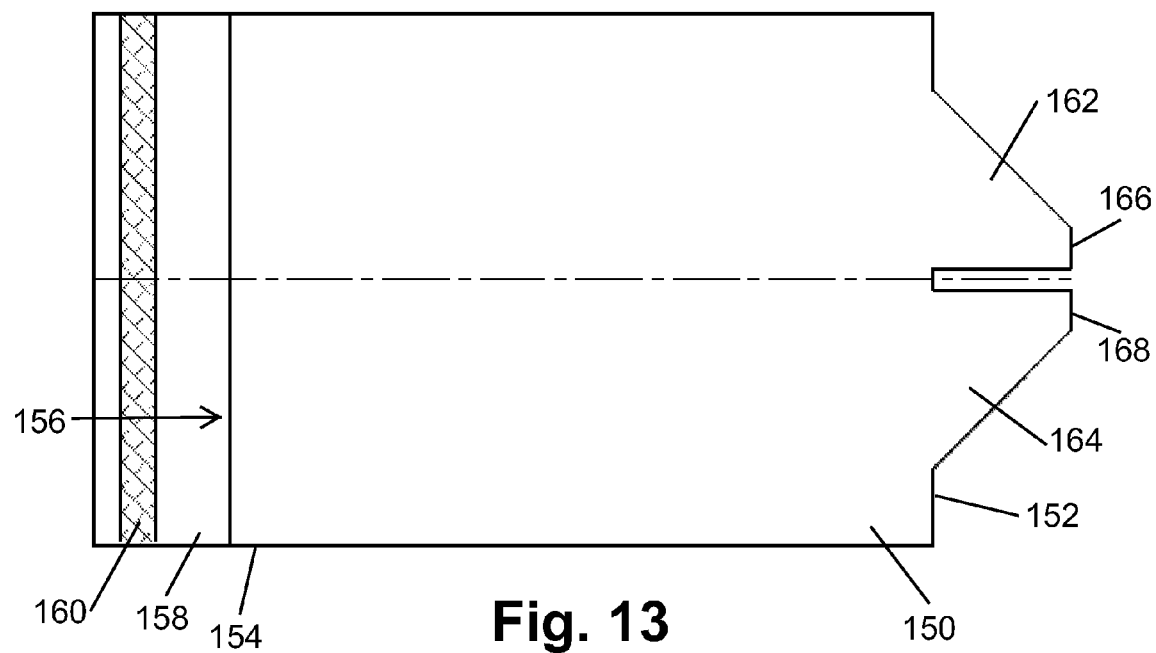
FIG. 13 depicts an embodiment of the present polymeric bags suitable for use with some embodiments of the present devices.

FIG. 13 depicts a polymeric bag 150 that is configured to fit around device 19 to reduce and/or prevent contamination of device 19 during use. In the embodiment shown, bag 150 has a first end 152 and a second end 154. Second end 154 includes an opening 156 and a flap 158 comprising an (e.g., pressure-sensitive) adhesive 158. Bag 150 is configured to permit device 19 to be inserted through opening 156 such that flap 158 can be folded over to cover opening 156 and adhesive 160 will hold flap 158 over opening 156. First end 152 includes extended portions 162 and 164 configured to permit connectors 46 and 52 to extend out of bag 150 when device 19 is disposed in bag 150 (e.g., during operation of device 19 and/or protruder 10). More particularly, in the embodiment shown, extended portion 162 includes a hole hole 166 configured to permit connector 46 to extend out of hole 166, and extended portion 164 has a hole 168 configured to permit connectors 52 to extend out of through hole 168. Polymeric bag 150 can comprise, for example, a plastic or other liquid-and/or gas-impermeable material that is configured to reduce contaminate of device 19 and/or protruder 10 generally, such as with body fluids and/or the like. In the embodiment shown, bag 150 is disposable (e.g., after a single use) and is a single-use bag.

Alternatively or additionally, some embodiments can comprise: a polymeric bag (not shown), configured to fit around at least one (e.g., both) of upper dental appliance 18 and lower dental appliance 20, and/or two bags each configured to fit around one of upper dental appliance 18 and lower dental appliance 20. In some embodiments, the polymeric bag is configured to fit between dental impression material and the at least one of upper dental appliance 18 and lower dental appliance 20. In some embodiments, a polymeric bag is configured to fit around device 19. Some embodiments of the present methods comprise disposing a positioning device (e.g., 19) in a polymeric bag (e.g., 150) such that a drive-motor connector (e.g., 46) and/or an adjustment-mechanism connector (e.g., 52) extend out of the polymeric bag; coupling an upper mounting bracket (e.g., 12) having an upper dental appliance (e.g., 18) to one of the drive-motor connector and the adjustment-mechanism connector, and a lower mounting bracket (e.g., 14) having a lower dental appliance (e.g., 20) to the other of the drive-motor connector and the adjustment-mechanism connector (e.g., such that the upper mounting bracket and lower mounting bracket are coupled by a rail system (e.g., 22)); and/or actuating the device to displace a patient's mandible relative to the patient's maxilla.

Figure 14A:
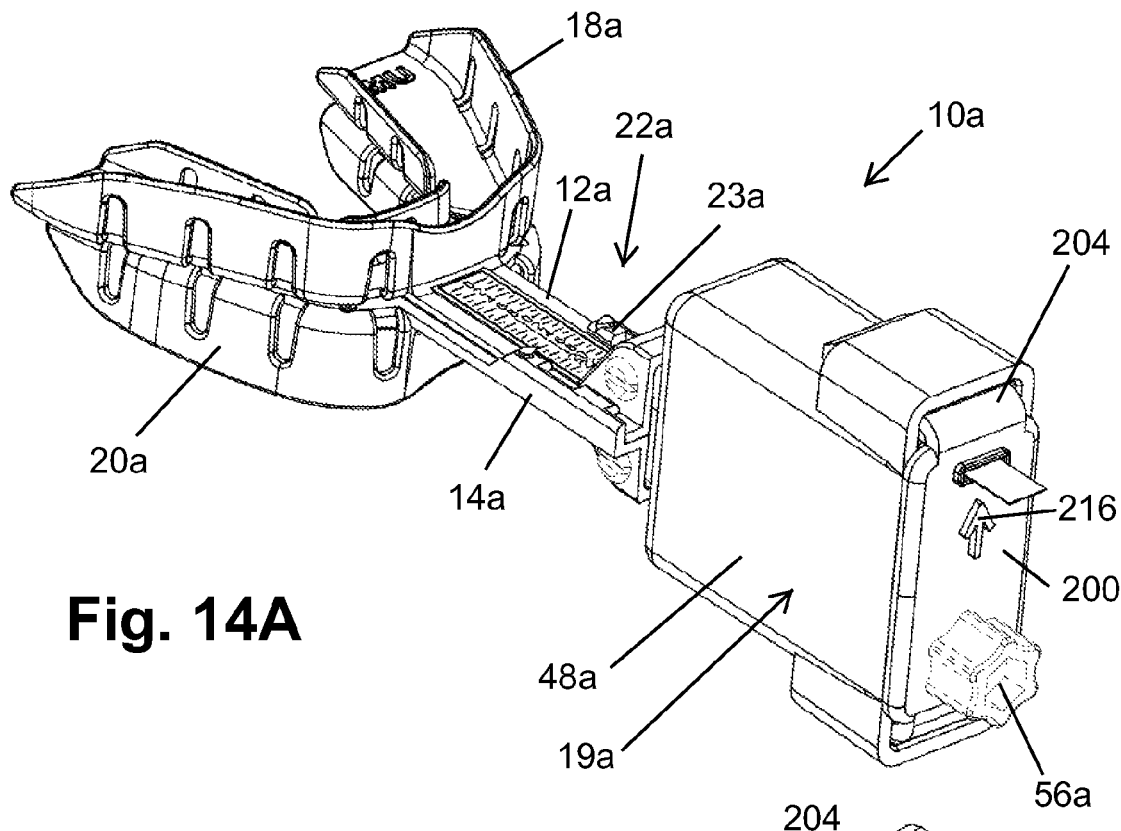
FIGS. 14A-14B are perspective views of another embodiment of the present mandibular protruders.
Figure 14B:
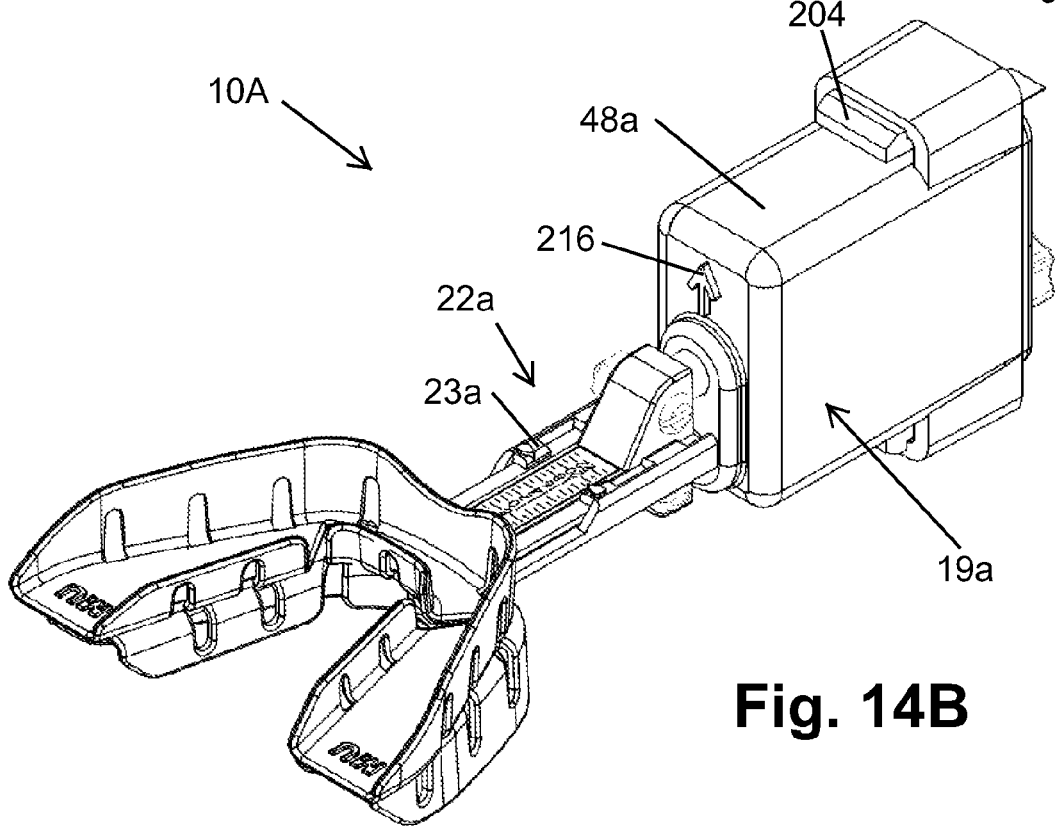
Figure 14C:
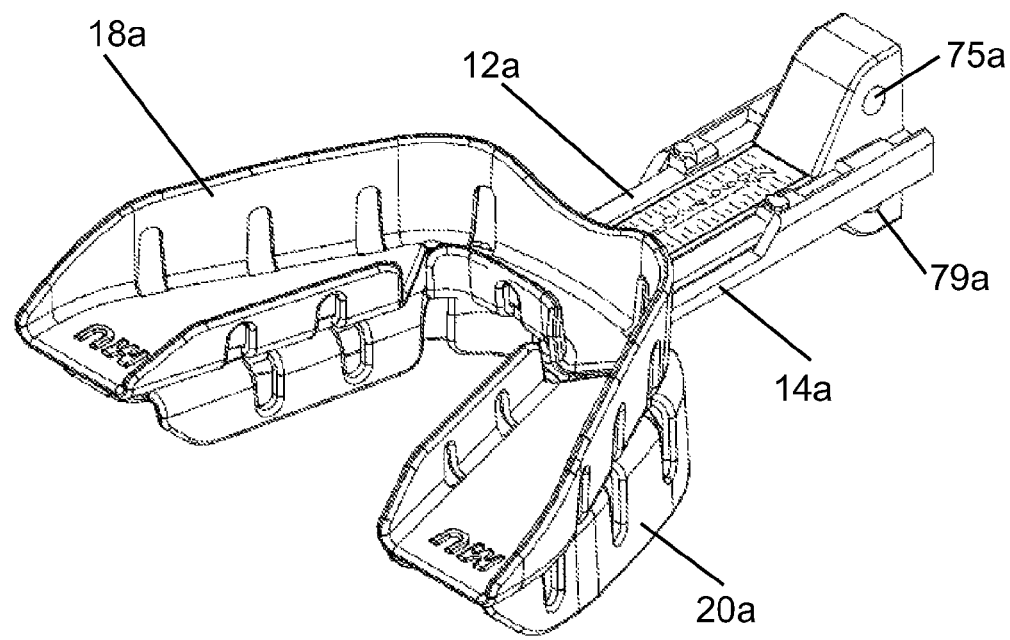
FIGS. 14C-14D are enlarged perspective and side views, respectively, of an upper mounting bracket and lower mounting bracket of the protruder of FIGS. 14A-14B.
Figure 14D:
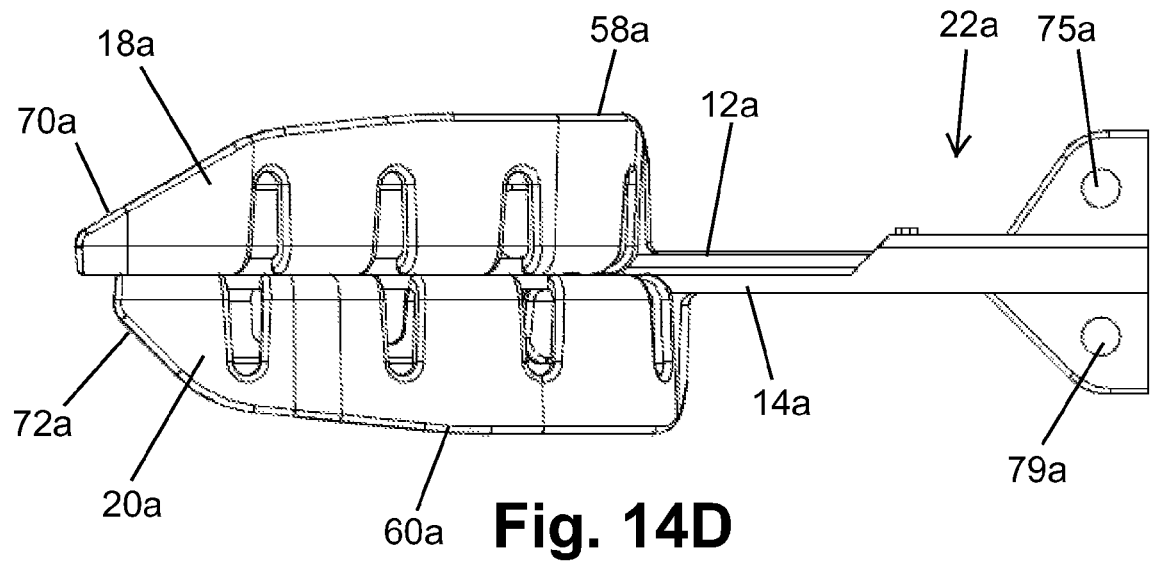
Figure 14E:
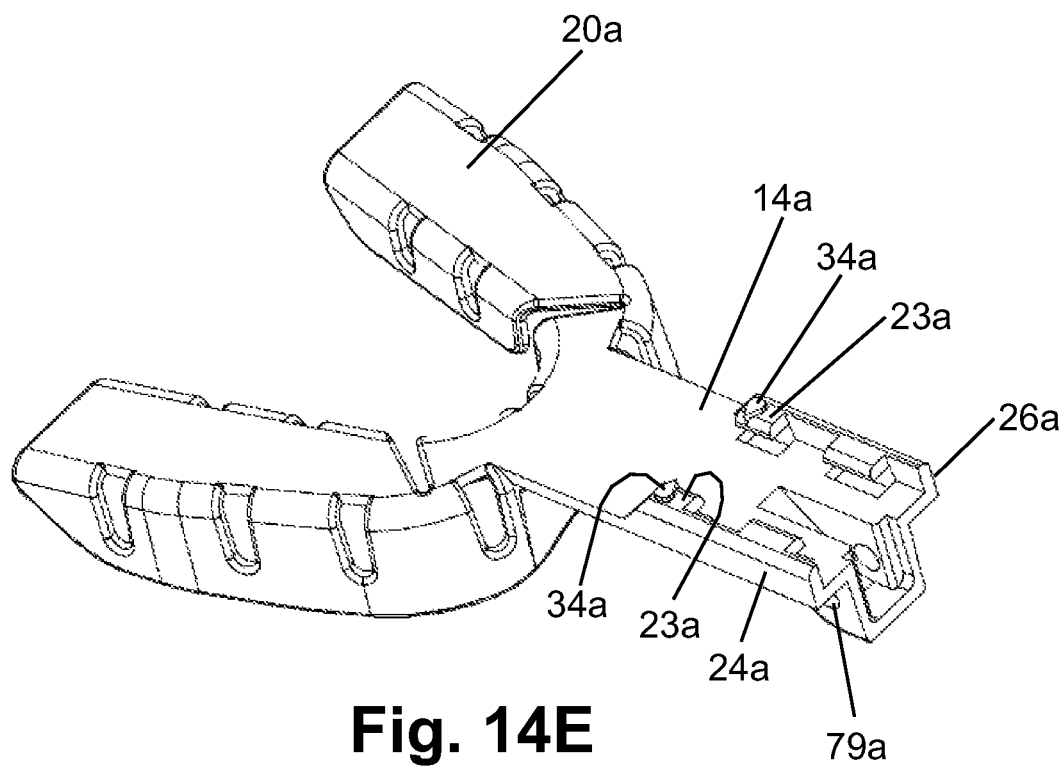
FIG. 14E is a top perspective view of the lower mounting bracket of the protruder of FIGS. 14A-14B.
Figure 14F:
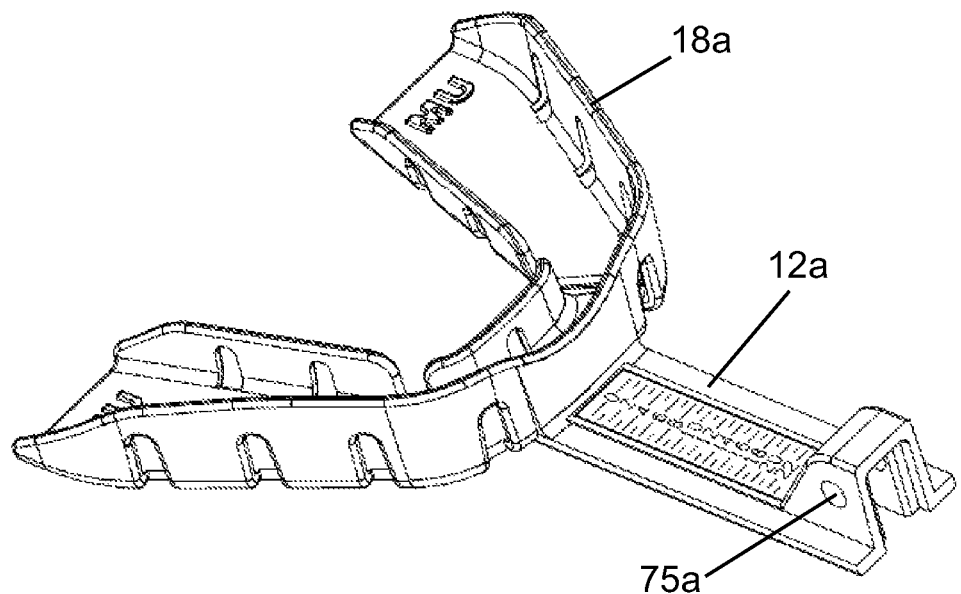
FIG. 14F is a top perspective view of the upper mounting bracket of the protruder of FIGS. 14A-14B.

FIGS. 14A and 14B depict an alternate embodiment 10A of the present protruders. FIGS. 14C-14F depict upper mounting bracket 12a and lower mounting bracket 14a of protruder 10a. Protruder 10a is substantially similar to protruder 10, above, except where noted. Components of protruder 10a are numbered similarly to similar components of protruder 10 (e.g., connector 46a and connector 46), and such similarly numbered components are substantially similar, except where otherwise noted. The description of protruder 10a will therefore focus on the differences between protruder 10a and protruder 10. FIG. 14F depicts a cross-sectional view of alternate housing 48a.

In the embodiment shown, rail system 22a (e.g., guides 23a) is spaced apart from upper dental appliance 18a and lower dental appliance 20a. More particularly, at least one of (e.g., both of upper mounting bracket 12a and lower mounting bracket 14a includes an elongated planar portion (e.g., elongated planar portion of upper mounting bracket 12 that extends from upper dental appliance 18a to the end of bracket 12 that couples to connector 46a) having a length, and rail system 22a has a length that is less than (e.g., less than 30, 40, 50, 60, 70, 80, 90 percent of) the length of the elongated planar portion. In the embodiment shown, rail system 22 has a length that is less than Additionally, in the embodiment shown, housing 48a includes a back portion 200 that is openable or removable by way of clips 204 that are configured to extend through openings 208. Housing 48a is also configured to include enlarged portions 212 and 214 adjacent to the holes through which connectors 46a and 52a extend. In the embodiment shown, enlarged portions 212 and 214 are larger than the respective holes, and are configured to receive a seal between housing 48a and respective connectors 46a and 52a.

In the embodiment shown, one or more (e.g., two) pointers 34a are each coupled to (e.g., integral with) the top of a guide 23a, such that, for example, the pointer need not extend beyond or be disposed between the guide 23a closes to trays 58a and 60a, thereby permitting a reduction in the length of rail system 22a. Additionally, in the embodiment shown, the upwardly extending portion (through which hole 75a passes) of upper mounting bracket 12a that is configured to be coupled to connector 46a has a maximum width that is less than the distance between the inner edges of opposing guides 23a of rail system 22 (guides 23a on opposite sides of upper mounting bracket 12a). Similarly, in the embodiment shown, the downwardly extending portion (through which hole 79a passes) of lower mounting bracket 14a that is configured to be coupled to connector 52a also has a maximum width that is less than the distance between the inner edges of opposing guides 23a of rail system 22a (guides 23a on opposite sides of upper mounting bracket 12a). In contrast, protruder 10, above, is configured such that the upwardly extending portion (through which hole 75 passes) of upper mounting bracket 12 that is configured to be coupled to connector 46 has a maximum width that is greater than the distance between the inner edges of opposing guides 23 of rail system 22; and such that the downwardly extending portion (through which hole 79 passes) of lower mounting bracket 14 that is configured to be coupled to connector 52 has a maximum width that is greater than the distance between the inner edges of opposing guides 23 of rail system 22.

In the embodiment shown, lateral portions 70a and 72a of upper dental appliance 18a (tray 58a) and lower dental appliance 20a (tray 60a) are relatively shorter than lateral portions 70 and 72 of trays 58 and 60, respectively. More particularly, trays 58a and 60a are configured to receive a patient's upper and lower teeth, respectively, such that at least one of lateral portions 70a and 72a terminate anterior to (e.g., extend no further back than) one or more of the patient's molars (e.g., third molar, second molar, and/or first molar). In the embodiment shown, device 19a (e.g., housing 48a, as shown) comprises one or more (two, as shown) indicators 216 that indicate which side of device 19a should face upwards during use, and thereby which of connectors 46 and 52 should correspond to upper mounting bracket 12.

Figure 14G:
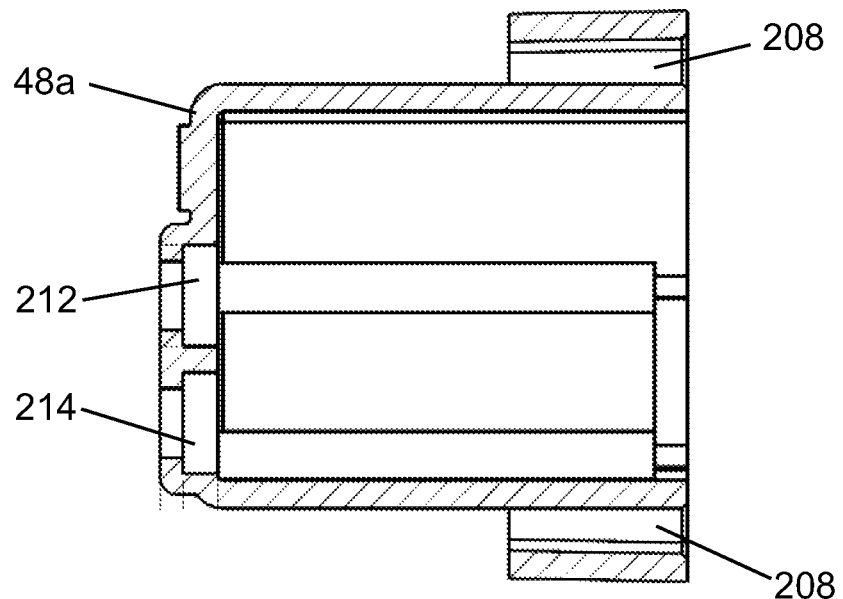
FIG. 14G is a cross-section of a housing of the protruder of FIGS. 14A-14B.
Figure 14H:
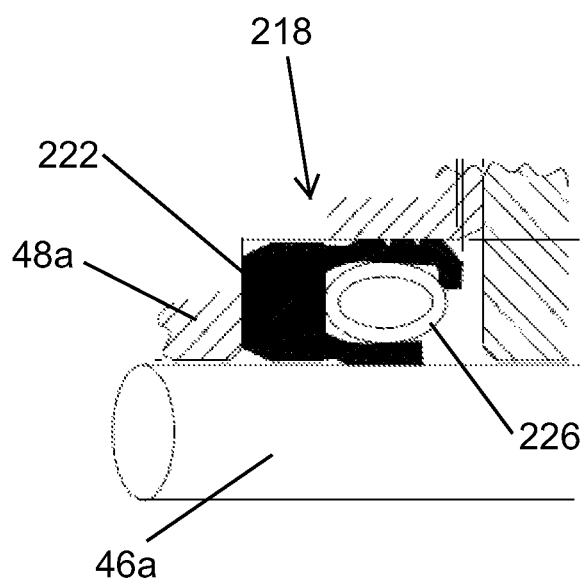
FIG. 14H is a cross-sectional view of a seal suitable for use in some embodiments of the present mandibular protruders.
Figure 15A:
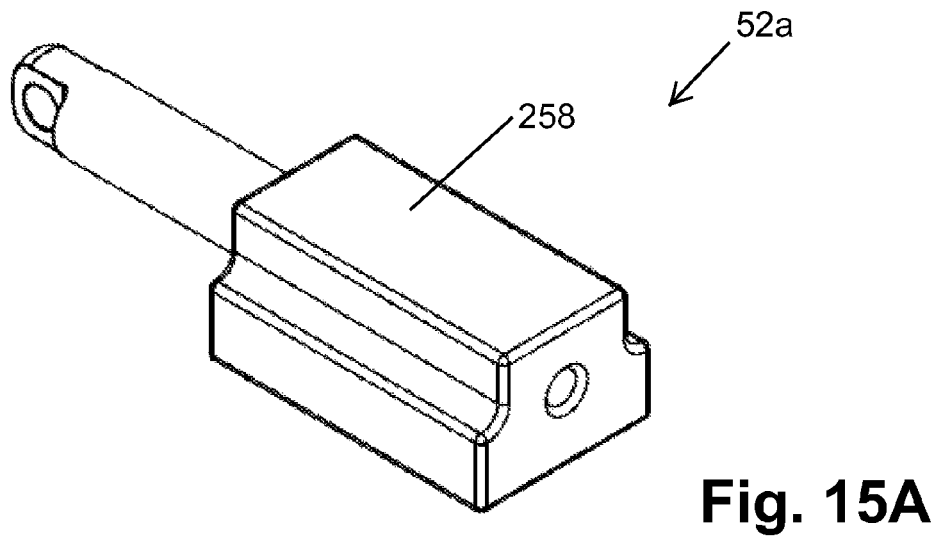
FIGS. 15A-15D are various views of an adjustment-mechanism connector or rod suitable for use in embodiments of the present protruders.
Figure 15B:
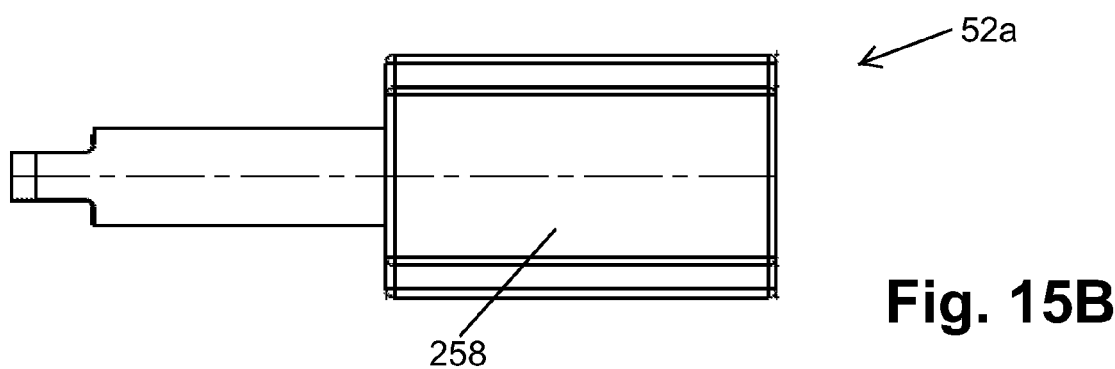
Figure 15C:
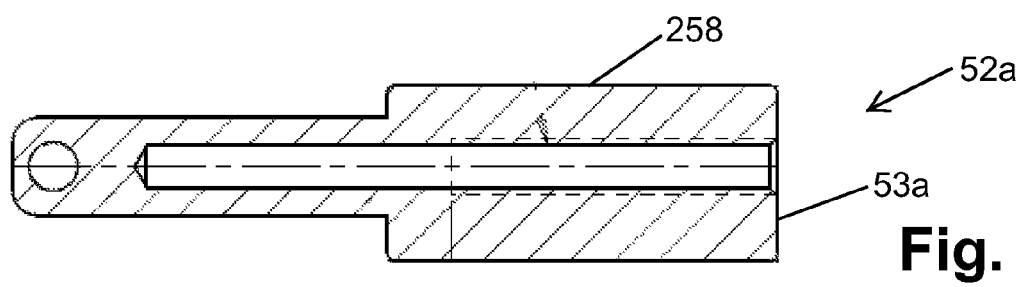
Figure 15D:
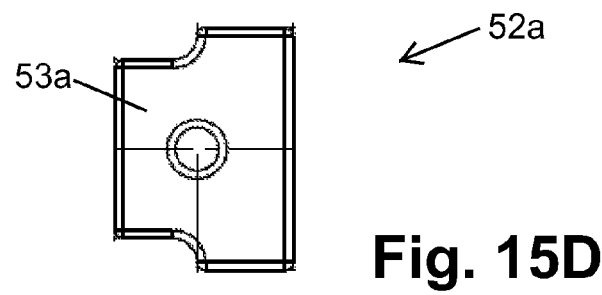

FIG. 14H illustrates cross-sectional view of a seal 218 suitable for use in some embodiments of the present mandibular protruders (e.g., 10). In the embodiment shown, housing 48a (see also FIG. 14G) is sectioned parallel to the longitudinal axis of connector 46a, however, seal 218 is also suitable for use around connector 52a. For example, in the embodiment shown, protruder 10a comprises a first seal 218 disposed around drive-motor connector 46a between housing 48a and drive-motor connector 46a (as shown, in enlarged portion 212); and a second seal 218 disposed around adjustment-mechanism connector 52a between housing 48a and adjustment-mechanism connector 52 (as shown, in enlarged portion 214). In the embodiment shown, seal 218 is donut-shaped (such that connector 46 extends through the center opening) and comprises a seal body 222 and a coil spring 226 coupled to seal body 222. More particularly, seal body 222 comprises an annular opening (e.g., around connector 46a, as shown) into which coil spring 226 is received. In the embodiment shown, coil spring 226 has an oval-shaped cross-section. Seal 218 may comprise a U-N130 series seal available from BAL SEAL ENGINEERING, U.S.A., and may be referred to by BAL SEAL by part number X572322.

FIGS. 15A-15D depict various views of an adjustment-mechanism connector or rod 52a suitable for use in embodiments of the present protruders (e.g., 10a). Connector 52a is substantially similar to connector 52, above, except where noted. The description of connector 52a will therefore focus on the differences between connector 52a and connector 52. Connector 52a comprises an enlarged portion 258). Portion 258 has a length that is equal to, between, or less than any 30, 40, 50, 60, 70, 80, 90 percent of the overall length of connector 52a. In the embodiment shown, enlarged portion 258 has a cross-section that is larger than the cross-section of the relatively smaller portion of connector 52a that extends out of housing 48a. Enlarged portion 258 is thus configured to limit the displacement of connector 52a relative to housing 48a because enlarged portion 258 is too large to exit housing 48a during actuation of the adjustment mechanism. In the embodiment shown, connector 52a includes longitudinal protrusions 55a that extend the full length of enlarged portion 258.

Figure 16A:
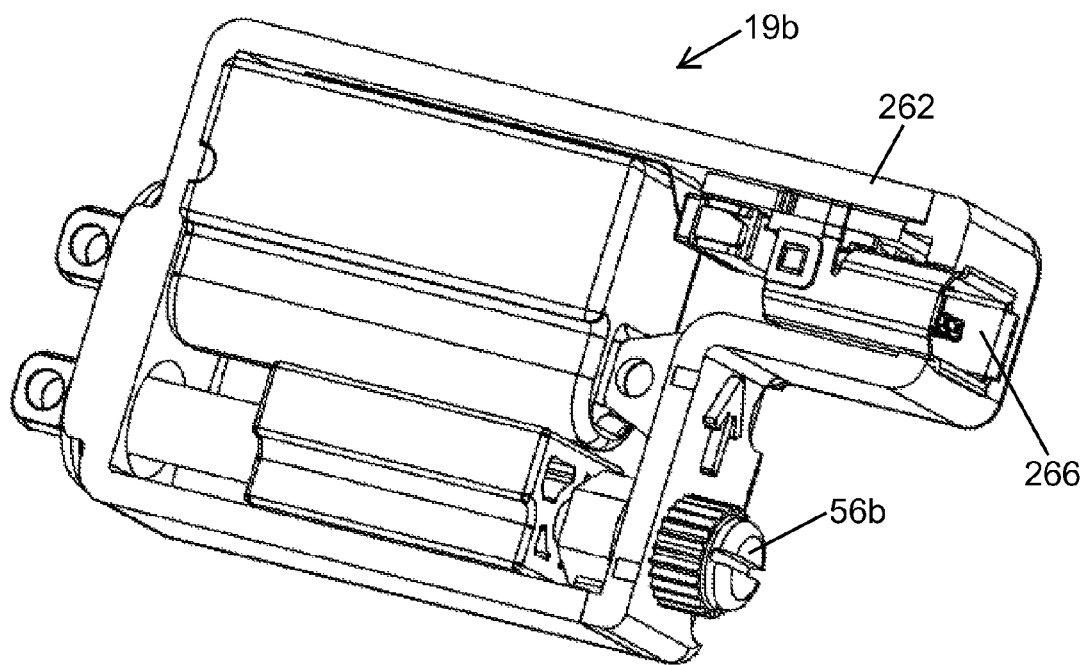
FIGS. 16A-16B are cutaway-perspective and side cross-sectional views, respectively, of another embodiment of the present positioning devices.
Figure 16B:
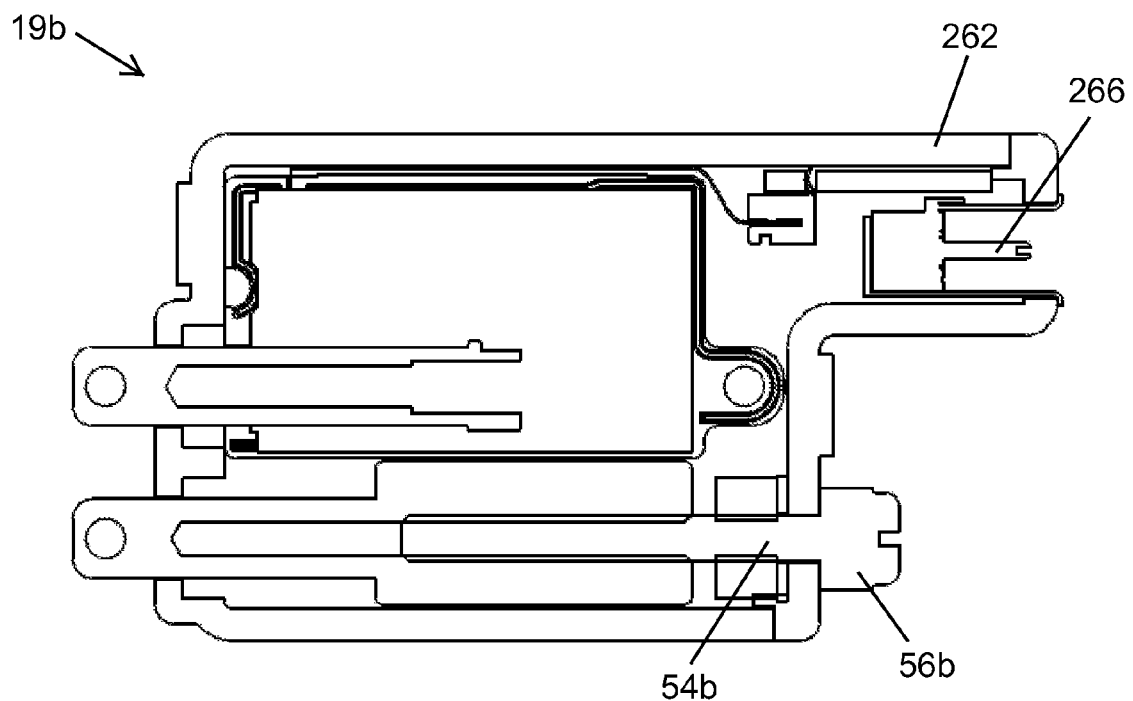
Figure 16C:
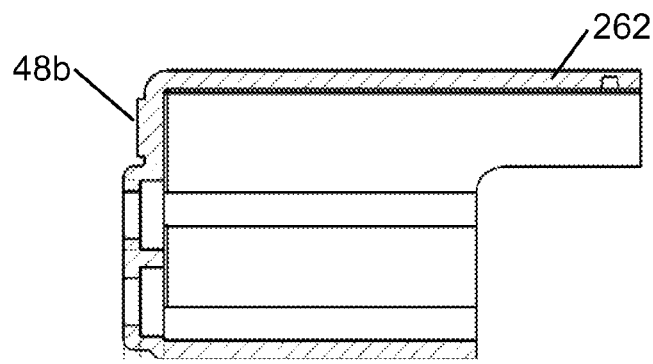
FIG. 16C is a cross-sectional view of a portion of a housing of the positioning device of FIGS. 16A-16B.

FIGS. 16A-16B are cutaway-perspective and side cross-sectional views, respectively, of another embodiment 19b of the present positioning devices. Device 19b is substantially similar to device 19a, above, except where noted. Components of device 19b are numbered similarly to similar components of device 19a (e.g., connector 46b and connector 46a), and such similarly numbered components are substantially similar, except where otherwise noted. The description of device 19b will therefore focus on the differences between device 19b and device 19a. FIG. 16C depicts a cross-sectional view of housing 48b. Housing 48b of device 19b includes a protruded portion 262 that is configured to receive a plug 266 (e.g., a female plug, as shown). Female plug 266 is wired to drive motor 16 such that a male plug (not shown) can be removably coupled to female plug 266 to apply voltage and/or send control signals to drive motor 16 (e.g., from controller 94 and/or workstation 92). Additionally, in the embodiment shown, device 19b includes an enlarged knob 56b that is configured to be turned by hand (e.g., knob 56b has a transverse dimension that is at least twice as large as the diameter of screw 54b.

Figure 17A:
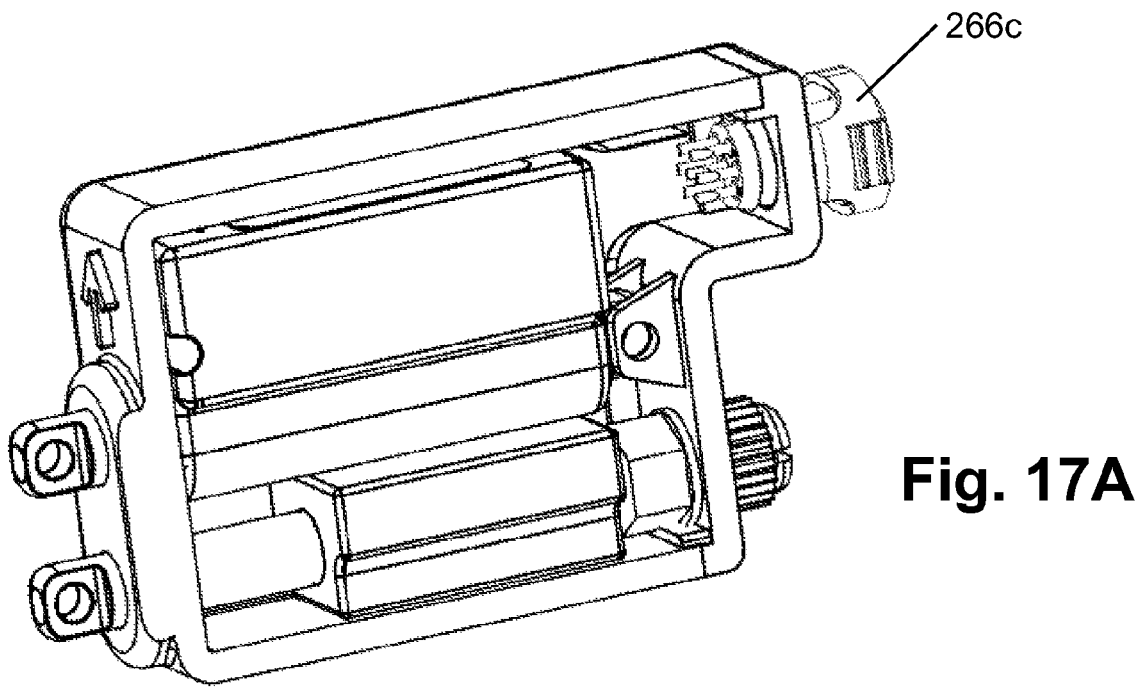
FIG. 17A is a cutaway perspective view of another embodiment of the present positioning devices.
Figure 17B:
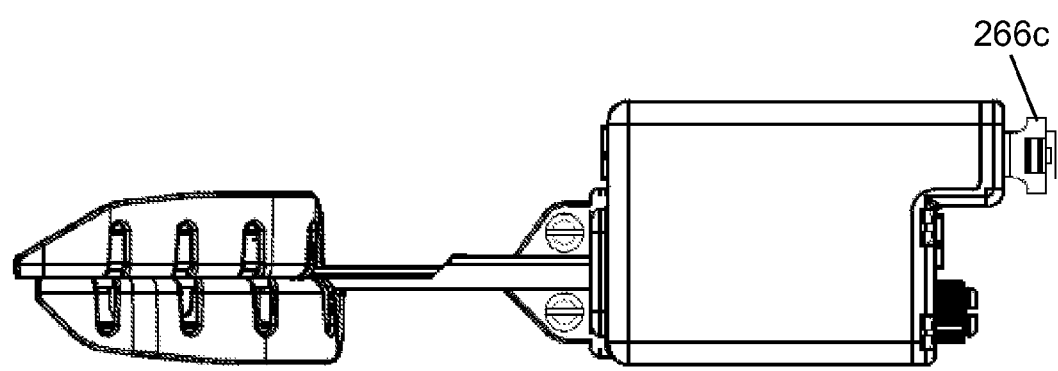
FIG. 17B is a side view of another embodiment of the present protruders that includes the positioning device of FIG. 17A.

Referring now to FIGS. 17A-17B, FIG. 17A is a cutaway perspective view of another embodiment 19c of the present positioning devices; and FIG. 17B is a side view of another embodiment of the present protruders 10c that includes positioning device 19c. Device 19c is substantially similar to device 19b, with the exception that plug 266c of device 19c has a circular configuration in which a plurality of pins are arranged in a circular shape.

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A mandibular protruder comprising,
an upper mounting bracket having an upper dental appliance and a portion that extends from the upper dental appliance, the upper dental appliance being configured for use with dental impression material;
a lower mounting bracket having a lower dental appliance and a portion that extends from the lower dental appliance, the lower dental appliance being configured for use with dental impression material;
wherein at least a portion of each extending portion is configured to extend outside the mouth of a subject when the upper and lower dental appliances are positioned in the mouth of the subject;
a rail system coupling the extending portions such that relative motion of the extending portions is substantially prevented in a lateral direction, wherein the rail system comprises an engaged portion of the upper and lower extending portions; and
wherein the upper mounting bracket or the lower mounting bracket is configured to be coupled to a drive-motor connector of a drive motor, the drive-motor connector having a longitudinal axis that is substantially parallel to the direction of actuation of the drive motor, such that the longitudinal axis of the upper mounting bracket or the lower mounting bracket is substantially parallel to the longitudinal axis of the drive-motor connector.

2. A mandibular protruder comprising,
an upper mounting bracket having an upper dental appliance and a portion that extends from the upper dental appliance, the upper dental appliance being configured for use with dental impression material;
a lower mounting bracket having a lower dental appliance and a portion that extends from the lower dental appliance, the lower dental appliance being configured for use with dental impression material;
wherein at least a portion of each extending portion is configured to extend outside the mouth of a subject when the upper and lower dental appliances are positioned in the mouth of the subject;
a rail system coupling the extending portions such that relative motion of the extending portions is substantially prevented in a lateral direction, wherein the rail system comprises an engaged portion of the upper and lower extending portions; and
wherein the rail system comprises a portion of one of the lower mounting bracket and the upper mounting bracket that is configured to wrap around a portion of the other of the lower mounting bracket and the upper mounting bracket.

3. The mandibular protruder of claim 2, wherein the portion of one of the upper mounting bracket and the lower mounting bracket that is configured to wrap around the other of the upper mounting bracket and the lower mounting bracket is a portion of the lower mounting bracket that is configured to wrap around a portion of the upper mounting bracket.

4. The mandibular protruder of claim 3, wherein the portion of the lower mounting bracket that is configured to wrap around the portion of the upper mounting bracket is coupled in fixed relation to the lower mounting bracket, and is configured to slidably engage the upper mounting bracket.

5. A mandibular protruder comprising,
an upper mounting bracket having an upper dental appliance and a portion that extends from the upper dental appliance, the upper dental appliance being configured for use with dental impression material;
a lower mounting bracket having a lower dental appliance and a portion that extends from the lower dental appliance, the lower dental appliance being configured for use with dental impression material;
wherein at least a portion of each extending portion is configured to extend outside the mouth of a subject when the upper and lower dental appliances are positioned in the mouth of the subject;
a rail system coupling the extending portions such that relative motion of the extending portions is substantially prevented in a lateral direction, wherein the rail system comprises an engaged portion of the upper and lower extending portions; and
a drive motor configured to effect relative displacement of the lower mounting bracket and the upper mounting bracket.

6. The mandibular protruder of claim 5, further comprising:
a plug coupled to the drive motor, and configured to be removably coupled to an external plug to provide a voltage to the drive motor.

7. The mandibular protruder of claim 5, further comprising:
a controller configured to transmit signals to the drive motor to cause the drive motor to effect relative displacement of the lower mounting bracket and the upper mounting bracket.

8. The mandibular protruder of claim 7, wherein the controller is configured to sense the relative position of the lower mounting bracket and the upper mounting bracket, and to transmit one or more signals indicative of the position of the lower mounting bracket relative to the upper mounting bracket.

9. The mandibular protruder of claim 5, wherein the drive motor comprises a linear actuator.

10. The mandibular protruder of claim 5,
further comprising:
an initial position adjustment mechanism configured to be actuated to adjust the relative position of the lower mounting bracket and the upper mounting bracket independently of the drive motor.

11. The mandibular protruder of claim 10, further comprising:
a housing coupled to the drive motor and the initial position adjustment mechanism;
wherein the drive motor is configured to adjust the position of one of the upper mounting bracket and the lower mounting bracket relative to the housing; and
wherein the initial position adjustment mechanism is configured to be actuated to adjust the position of the other of the upper mounting bracket and the lower mounting bracket relative to the housing.

12. A method comprising:
providing a mandibular protruder comprising:
an upper mounting bracket having an upper dental appliance and a portion that extends from the upper dental appliance;
a lower mounting bracket having a lower dental appliance and a portion that extends from the lower dental appliance, wherein at least a portion of each extending portion is configured to extend outside the mouth of a subject when the upper and lower dental appliances are positioned in the mouth of the subject;
a rail system coupling the extending portions such that relative motion of the extending portions is substantially prevented in a lateral direction;
a drive motor configured to effect relative displacement of the lower mounting bracket and the upper mounting bracket; and
an initial position adjustment mechanism configured to be actuated to adjust the relative position of the lower mounting bracket and the upper mounting bracket independently of the drive motor;
actuating the initial position adjustment mechanism to adjust the relative position of the upper mounting bracket and the lower mounting bracket; and
relatively displacing with the drive motor the upper mounting bracket and the lower mounting bracket when a patient's upper teeth are coupled to the upper dental appliance and the patient's lower teeth are coupled to the lower dental appliance to cause relative displacement between the upper dental appliance and the lower dental appliance and displace the patient's mandible relative to the patient's maxilla.

13. The method of claim 12, further comprising:
monitoring one or more characteristics of the patient while the patient sleeps;
wherein the relative displacement reduces the one or more characteristics.

14. The method of claim 13, further comprising:
determining an optimal mandibular displacement for the patient at which at least one of the one or more characteristics is minimized.

15. The method of claim 14, further comprising;
providing an oral appliance; and
adjusting the oral appliance to cause a mandibular displacement if worn by the patient that corresponds to the optimal mandibular displacement.

16. A method comprising:
providing a mandibular protruder comprising:
an upper mounting bracket having an upper dental appliance and a portion that extends from the upper dental appliance;
a lower mounting bracket having a lower dental appliance and a portion that extends from the lower dental appliance, wherein at least a portion of each extending portion is configured to extend outside the mouth of a subject when the upper and lower dental appliances are positioned in the mouth of the subject; and
a rail system that substantially restricts the relative motion of the extending portions in a lateral or vertical direction;
a drive motor configured to effect relative displacement of the lower mounting bracket and the upper mounting bracket; and
an initial position adjustment mechanism configured to be actuated to adjust the relative position of the lower mounting bracket and the upper mounting bracket independently of the drive motor;
actuating the initial position adjustment mechanism to adjust the relative position of the upper mounting bracket and the lower mounting bracket; and
relatively displacing with the drive motor the upper mounting bracket and the lower mounting bracket when a patient's upper teeth are coupled to the upper dental appliance and the patient's lower teeth are coupled to the lower dental appliance to cause relative displacement between the upper dental appliance and the lower dental appliance and displace the patient's mandible relative to the patient's maxilla.

* * * * *